(12) United States Patent
McFadden et al.

(10) Patent No.: US 7,585,507 B2
(45) Date of Patent: Sep. 8, 2009

(54) NUCLEIC ACID MOLECULES AND POLYPEPTIDES FOR IMMUNE MODULATION

(75) Inventors: Grant McFadden, London (CA); Karim Essani, Kalamazoo, MI (US)

(73) Assignee: Viron Therapeutics Inc., London (CA)

( * ) Notice: Subject to any disclaimer, the term of this patent is extended or adjusted under 35 U.S.C. 154(b) by 39 days.

(21) Appl. No.: 11/124,786

(22) Filed: May 9, 2005

(65) Prior Publication Data

US 2006/0286125 A1    Dec. 21, 2006

Related U.S. Application Data

(62) Division of application No. 09/976,605, filed on Oct. 11, 2001, now Pat. No. 6,894,155.

(60) Provisional application No. 60/239,354, filed on Oct. 11, 2000.

(51) Int. Cl.
*A61K 39/275* (2006.01)
*A61K 38/16* (2006.01)

(52) U.S. Cl. .................... 424/186.1; 424/232.1; 514/12

(58) Field of Classification Search ........................ None
See application file for complete search history.

(56) References Cited

U.S. PATENT DOCUMENTS

| 5,651,972 | A  | 7/1997  | Moyer et al.     |
|-----------|----|---------|------------------|
| 5,656,465 | A  | 8/1997  | Panicali et al.  |
| 5,686,409 | A  | 11/1997 | McFadden et al.  |
| 5,834,419 | A  | 11/1998 | McFadden et al.  |
| 5,871,740 | A  | 2/1999  | Smith            |
| 5,939,525 | A  | 8/1999  | McFadden et al.  |
| 6,495,515 | B1 | 12/2002 | McFadden et al.  |
| 6,559,298 | B1 | 5/2003  | Torigoe et al.   |
| 6,562,376 | B2 | 5/2003  | Hooper et al.    |
| 6,589,764 | B1 | 7/2003  | Sims et al.      |
| 6,589,933 | B1 | 7/2003  | McFadden et al.  |
| 6,605,280 | B1 | 8/2003  | Novick et al.    |
| 6,894,155 | B2 | 5/2005  | McFadden et al.  |
| 7,101,559 | B2 | 9/2006  | McFadden et al.  |
| 2002/0102535 | A1 | 8/2002 | McFadden et al. |
| 2004/0038203 | A1 | 2/2004 | McFadden et al. |
| 2009/0011979 | A1 | 1/2009 | McFadden et al. |

FOREIGN PATENT DOCUMENTS

| EP | 1034789 A1    | 9/2000  |
|----|---------------|---------|
| WO | WO 91/16431   | 10/1991 |
| WO | WO 92/17583   | 10/1992 |
| WO | WO 96/33730   | 10/1996 |
| WO | WO 97/11714   | 4/1997  |
| WO | WO 97/44054   | 11/1997 |
| WO | WO 00/12555   | 3/2000  |
| WO | WO 01/07480   | 2/2001  |
| WO | WO 01/62285   | 8/2001  |
| WO | WO 02/31115   | 4/2002  |
| WO | WO 02/32374   | 4/2002  |
| WO | WO 02/46214   | 6/2002  |
| WO | WO 02/060479  | 8/2002  |
| WO | WO 02/092008  | 11/2002 |

OTHER PUBLICATIONS

Alcami A. et al. Poxviruses: Capturing Cytokines and Chemokines. Seminars in Virology, 1998; 8(5):419-427.*
Essani, et al. Multiple anti-cytokine activities secreted from tanapox virus-infected cells. Microbial Pathogenesis. 1994;17:347-353.*
Alcami, et al. Blockade of Chemokine Activity by a Soluble Chemokine Binding Protein from Vaccinia Virus. J. Immunol. 1998, 160:624-633.*
Ahuja et al., "Chemokine Receptors and Molecular Mimicry," *Immunol. Today* 15:281 (1994).
Alcami et al., "Soluble Interferon-Gamma Receptors Encoded by Poxviruses," *Comp. Immunol. Microbiol. Infect. Dis.* 19:305 (1996).
Alcami et al., "Vaccinia, Cowpox, and Camelpox Viruses Encode Soluble Gamma Interferon Receptors with Novel Broad Species Specificity," *J. Virol.* 69:4633 (1995).
Alcami et al., "Receptors for Gamma-Interferon Encoded by Poxviruses: Implications for the Unknown Origin of Vaccinia Virus," *Trends Microbiol.* 4:321 (1996).
Amano et al., "Identification and Characterization of the Thymidine Kinase Gene of Yaba Virus," *J. Gen. Virol.* 76:1109 (1995).
Baringa, "Viruses Launch Their Own Star Wars," *Science* 258:1730 (1992).
Brunetti et al., "A Secreted High-Affinity Inhibitor of Human TNF from Tanapox Virus," *Proc. Natl. Acad. Sci. U.S.A.* 100:4831-4836 (2003).
Chaudhuri et al., "Expression of the Duffy Antigen in K562 Cells," *J. Biol. Chem.* 269:7835 (1994).
Elsner et al., "Eotaxin-2 Activates Chemotaxis-Related Events and Release of Reactive Oxygen Species via Pertussis Toxin-Sensitive G Proteins in Human Eosinophils," *Eur. J. Immunol.* 28:2152 (1998).
Endres et al., "CD4-Independent Infection by HIV-2 is Mediated by Fusin-CXCR4," *Cell* 87:745 (1996).
Essani et al., "Multiple Anti-Cytokine Activities Secreted from Tanapox Virus-Infected Cells," *Microbial. Pathogenesis* 17:347-353 (1994).

(Continued)

*Primary Examiner*—Mary E Mosher
*Assistant Examiner*—Stuart W Snyder
(74) *Attorney, Agent, or Firm*—Clark & Elbing LLP; Kristina Bieker-Brady

(57) ABSTRACT

The invention provides gp38 polypeptides, which play a role in immunomodulation, nucleic acid molecules encoding these polypeptides, and therapeutic and diagnostic methods employing these polypeptides and nucleic acid molecules. The invention also provides methods for identifying compounds that modulate the biological activities of gp38 nucleic acid molecules and polypeptides, and therapeutic methods employing these compounds.

49 Claims, 9 Drawing Sheets

OTHER PUBLICATIONS

Fenger et al., "Proteins of Yaba Monkey Tumor Virus I Structural Proteins," *J. Virol.* 18:757 (1976).
Gene Bank Sequence, AB015885.
Gene Bank Sequence, AF153912.
Gene Bank Sequence, AJ293568.
Gene Bank Sequence, D26580.
Graham et al., "Myxoma Virus M11L ORF Encodes a Protein for which Cell Surface Localization is Critical in Manifestation of Viral Virulence," *Virol.* 191:112 (1992).
Graham et al., "The T1-35kDa Family of Poxvirus-Secreted Proteins Bind Chemokines and Modulate Leukocyte Influx into Virus-Infected Tissues," *Virol.* 229:12 (1997).
Hoffman et al., "Chemokine Regulation of CNS T-Cell Infiltration in Experimental Autoimmune Encephalomyelitis," *Research in Immunology* 149:790 (1998).
Horuk et al., "Molecular Properties of the Chemokine Receptor Family," *TIPS* 15:159 (1994).
Hu et al., "Cowpox Virus Contains Two Copies of an Early Gene Encoding a Soluble Secreted Form of the Type II TNF Receptor," *Virol.* 204:343 (1994).
Jackson et al., "Expression of Mouse Interlukin-4 by a Recombinant Ectromelia Virus Suppresses Cytolytic Lymphocyte Responses and Overcomes Genetic Resistance to Mousepox," *Virol.* 75:1205-1210 (2001).
Knight et al., "Studies on Tanapox Virus," *Virol.* 172:116 (1989).
Kotwal et al., "Regulation of Cytokine Secretion by Poxvirus Encoded Proteins," *Adv. In Exp. Med. and Biol.* 351:187, eds. Lindley, Westeick, and Kunkel, Plenum Press, NY (1992).
Lee et al, "The Genome Sequence of Yaba-Like Disease Virus, a Yatapoxvirus," *Virol.* 281:170 (2001).
Lee et al., "The Sequence of Yaba-Like Disease Virus, A Yatapoxvirus," 13th *Symposium International sur les Poxvirus et Iridovirus* (Sep. 2-6, 2000).
Lee et al, "Studies of Yaba-Like Disease Virus, a Yatapoxvirus," *University of Oxford, Thesis* pp. 15-27 and 191-239 (Sep. 25, 2000).
Lomas et al., "Inhibition of Plasmin, Urokinase, Tissue Plasminogen Activator, and $C_{1s}$ by a Myxoma Virus Serine Proteinase Inhibitor," *J. Biol. Chem.* 268:516 (1993).
Macen et al., "SERP1, a Serine Proteinase Inhibitor Encoded by Myxoma Virus, is a Secreted Glycoprotein that Interferes with Inflammation," *Virol.* 195:348 (1993).
McFadden, "Rabbit, Hare, Squirrel and Swine Poxviruses," *Encyclopedia of Virology* pp. 1153-1160 (1997).
McFadden et al., "Myxoma T2 Proteins as a Model for Poxvirus TNF Receptor Homologs," *J. Neuroimmunol.* 72:119 (1997).
McFadden et al., "Interruption of Cytokine Networks by Poxviruses: Lessons from Myxoma Virus," *J. Leukocyte Biol.* 57:731 (1995).
Mossman et al., "Myxoma Virus M-T7, a Secreted Homolog of the Interferon-Gamma Receptor, is a Critical Virulence Factor for the Development of Myxomatosis in European Rabbits," *Virol.* 215:17 (1996).
Mossman et al., "The Myxoma Virus-Soluble Interferon-Gamma Receptor Homolog, M-T7, Inhibits Interferon-Gamma in a Species Specific Manner," *J. Biol. Chem.* 270:3031 (1995).
Mossman et al., "Species Specificity of Ectromelia Virus and Vaccinia Virus Interferon-Gamma Binding Proteins," *Virol.* 208:762 (1995).
Mossman et al., "Interferon-γ Receptors Encoded by Poxviruses," *Viroreceptors, Virokines And Related Immune Modulators Encoded by DNA Viruses* pp. 41-54 Ed: McFadden, R.G. Landers Co. (1994).
Neote et al., "Molecular Cloning, Functional Expression, and Signaling Characteristics of a C-C Chemokine Receptor," *Cell* 72:415 (1993).
Neurath et al., "Search for Hepatitis B Virus Cell Receptors Reveals Binding Sites for Interleukin 6 on the Virus Envelope Protein," *J. Exp. Med.* 175:461 (1992).
Olsen et al., "Immunodiffusion Analysis of Yaba Poxvirus Structural and Associated Antigens," *J. Virol.* 5:212 (1970).
Opgenorth et al., "Deletion of the Growth Factor Gene Related to EGF and TGFα Reduces Virulence of Malignant Rabbit Fibroma Virus," *Virol.* 186:175 (1992).

Opgenorth et al., "Deletion Analysis of Two Tandemly Arranged Virulence Genes in Myxoma Virus, M11L and Myxoma Growth Factor," *J. Virol.* 66:4720 (1992).
Opgenorth et al., "Transforming Growth Factor Alpha, Shope Fibroma Growth Factor, and Vaccinia Growth Factor can Replace Myxoma Growth Factor in the Induction of Myxomatosis in Rabbits," *Virol.* 192:701 (1993).
Paulose et al., "Selective Inhibition of TNF-α Induced Cell Adhesion Molecule Gene Expression by Tanapox Virus," *Microbial. Pathogenesis* 25:33-41 (1998).
Powell et al., "An I-Kappa-B Homolog Encoded by African Swine Fever Virus Provides a Novel Mechanism for Downregulation of Proinflammatory Cytokine Responses in Host Macrophages," *J. Virol.* 70:8527 (1996).
Riffkin et al., "A Single Amino-Acid Change between the Antigenically Different Extracellular Serine Proteases V2 and B2 from Dichelobacter Nodosus," *Gene* 167:279-283 (1995).
Schreiber et al., "The Myxoma Virus TNF-Receptor Homologue (T2) Inhibits Tumor Necrosis Factor-Alpha in a Species-Specific Fashion," *Virol.* 204:692 (1994).
Sedger et al., "M-T2: A Poxvirus TNF Receptor Homologue with Dual Activities," *Immunol. and Cell Biol.* 74:538 (1996).
Smith et al., "T2 Open Reading Frame from the Shope Fibroma Virus Encodes a Soluble Form of the TNF Receptor," *Biochem. Biophys. Res. Commun.* 176:335 (1991).
Smith, "Virus Proteins that Bind Cytokines, Chemokines or Interferons," *Curr. Opin. Immunol.* 8:467 (1996).
Symons et al., "Vaccinia Virus Encodes a Soluble Type I Interferon Receptor of Novel Structure and Broad Species Specificity," *Cell* 81:551 (1995).
Thompson, "Human Gene Therapy Harsh Lessons, High Hopes," *FDA Consumer Magazine* (Sep.-Oct. 2000).
Trkola et al., "CD4-Dependent, Antibody-Sensitive Interactions between HIV-1 and Its Co-Receptor CCR-5," *Nature* 384:184 (1996).
Upton et al., "Tumorigenic Poxviruses: Genomic Organization and DNA Sequence of the Telomeric Region of the Shope Fibroma Virus Genome," *Virol.* 160:20 (1987).
Upton et al., "Myxoma Virus Expresses a Secreted Protein with Homology to the Tumor Necrosis Factor Receptor Gene Family that Contributes to Viral Virulence," *Virol.* 184:370 (1991).
Upton et al., "Encoding of a Homolog of the IFN-Gamma Receptor by Myxoma Virus," *Science* 258:1369 (1992).
Upton et al., "Mapping and Sequence of a Gene from Myxoma Virus that is Related to those Encoding Epidermal Growth Factor and Transforming Growth Factor Alpha," *J. Virol.* 61:1271 (1987).
Upton et al., "Myxoma Virus and Malignant Rabbit Fibroma Virus Encode a Serpin-Like Protein Important for Virus Virulence," *Virol.* 179:618 (1990).
Upton et al., "Detection of Viral Homologs of Cellular Interferon Gamma Receptors," *Methods in Molecular Genetics* 4:383 (1994).
Vinyals et al., "Failure of Wild-Type p53 Gene Therapy in Human Cancer Cells Expressing a Mutant p53 Protein," *Gene Therapy* 6:22-33 (1999).
Wu et al., "CD4-Induced Interaction of Primary HIV-1 gp120 Glycoproteins with the Chemokine Receptor CCR-5," *Nature* 384:179 (1996).
McFadden, Mutational Analysis of TPV-2L, unpublished document.
Rahman et al., "Variation in Ligand Binding Specificities of a Novel Class of Poxvirus-encoded Tumor Necrosis Factor-binding Protein," *J. Biol. Chem.* 281(32):22517-22526 (2006), and supporting information (3 pages).
Supporting information (2 pages) for Brunetti et al., "A Secreted High-Affinity Inhibitor of Human TNF from Tanapox Virus," *Proc. Natl. Acad. Sci. U.S.A.* 100:4831-4836 (2003).
Alcami et al., "Blockade of Chemokine Activity by a Soluble Chemokine Binding Protein from Vaccinia Virus," *J. Immunol.* 160:624-633 (1998).
Alcami et al., "Poxviruses: Capturing Cytokines and Chemokines," *Sem. Virology* 8:419-427 (1998).
Born et al., "A Poxvirus Protein that Binds to and Inactivates IL-18, and Inhibits NK Cell Response.," *J. Immunol.* 164:3246-54 (2000).

Brunetti et al., "Complete Genomic Sequence and Comparitive Analysis of the Tumorigenic Poxvirus Yaba Monkey Tumor Virus," *J. Virol.* 77:13335-13347 (2003).

Calderara et al., "Orthopoxvirus IL-18 Binding Proteins: Affinities and Antagonist Activities," *Virology* 279:22-26 (2001).

Esteban and Buller, "Identification of Residues in an Orthopoxvirus Interleukin-18 Binding Protein Involved in Ligand Binding and Species Specificity," *Virology* 323:197-207 (2004).

Esteban et al., "Interleukin-18 and Glycosaminoglycan Binding by a Protein Encoded by Variola Virus," *J. Gen. Virol.* 85:1291-1299 (2004).

Gene Bank Sequence, AB018404.

Gene Bank Sequence, AB025319.

Gene Bank Sequence, AY253324.

McFadden and Murphy, "Host-Related Immunomodulators Encoded by Poxviruses and Herpesviruses," *Curr. Opin. Microbiol.* 3(4):371-378 (2000).

Moss et al., "Immune-Defense Molecules of *Molluscum Contagiosum* Virus, a Human Poxvirus," *Trends Microbiol.* 8:473-477 (2000).

Nazarian et al., "Yaba Monkey Tumor Virus Encodes a Functional Inhibitor of Interleukin-18," *J. Virol.* 82(1):522-8 (2008). [Epub Oct. 24, 2007].

Senkevich et al., "Genome Sequence of a Human Tumorigenic Poxvirus: Prediction of Specific Host Response-Evasion Genes," *Science* 273:813-816 (1996).

Senkevich et al., "The Genome of *Molluscum Contagiosum* Virus: Analysis and Comparison with Other Poxviruses," *Virology* 233:19-42 (1997).

Smith et al., "Ectromelia, Vaccinia and Cowpox Viruses Encode Secreted Interleukin-18-Binding Proteins," *J. Gen. Virol.* 81:1223-1230 (2000).

Symons et al., "The Vaccinia Virus C12L Protein Inhibits Mouse IL-18 and Promotes Virus Virulence in the Murine Intranasal Model," *J. Gen. Virol.* 83:2833-44 (2002).

Xiang and Moss, "Correspondence of the Functional Epitopes of Poxvirus and Human Interleukin-18-Binding Proteins," *J. Virol.* 75:9947-9954 (2001).

Xiang and Moss, "Determination of the Functional Epitopes of Human Interleukin-18-Binding Protein by Site-Directed Mutagenesis," *J. Biol. Chem.* 276:17380-17386 (2001).

Xiang and Moss, "Identification of Human and Mouse Homologs of the MC51L-53L-54L Family of Secreted Glycoproteins Encoded by the *Molluscum Contagiosum* Poxvirus," *Virology* 257:297-302 (1999).

Xiang and Moss, "IL-18 Binding and Inhibition of Interferon Gamma Induction by Human Poxvirus-Encoded Proteins," *Proc. Natl. Acad. Sci. U.S.A.* 96:11537-11542 (1999).

Xiang and Moss, "*Molluscum Contagiosum* Virus Interleukin-18 (IL-18) Binding Protein is Secreted as a Full-Length Form That Binds Cell Surface Glycosaminoglycans Through the C-Terminal Tail and a Furin-Cleaved Form with Only the IL-18 Binding Domain," *J. Virol.* 77:2623-30 (2003).

International Search Report for WO 02/031115 dated Mar. 15, 2002.

International Search Report for WO 02/046214 dated May 3, 2002.

\* cited by examiner

FIGURE 1

```
TPVgp38aa   1                            TLKYCYTVTLKDNGLYDKVFYCHYN         25
Yabagp38    1  MNKLILSLLGFVATCNCITLRYNYTVTVK-NGLYDGVFFDYYNDQLVTRI            49
                              **.* ****.* ***** **.   **

TPVgp38aa  26                25  (SEQ ID NO: 10)
Yabagp38   50  SYNHETKRGNVN  61  (SEQ ID NO: 11)
```

FIGURE 2

YMTV partial gp38 gene (183 nucleotide):

5'
ATGAATAAGTTAATTTTATCGTTGTTGGGTTTTGTGGCAACTTGCAATTGTATAACCTTAAGATATAATTATACCGTTA
CGGTAAAGAATGGATTATACGACGGGGTATTTTTTGATTATTACAACGATCAGTTAGTAACGAGGATATCATATAATCA
TGAAACCAAACGAGGAAATGTAAAT  (SEQ ID NO: 12)

YMTV partial gp38 gene (61 amino acid):

5'
MNKLILSLLGFVATCNCITLRYNYTVTVKNGLYDGVFFDYYNDQLVTRISYNHETKRGNVN (SEQ ID NO: 11)

SEQ ID NO: 4

MNKLILFSTIVAVCNCITLKYNYTVTLKDNGLYDGVFYDHYNDQLVTKISYNHETRHGNVNFRADWFNIS
RSPHTPGNDYNFNFWYSLMKETLEEINKNDSTKTTSLSLITGCYETGLLFGSYGYVETANGPLARYHTGD
KRFTKMTHKGFPKVGMLTVKNTLWKDVKTYLGGFEYMGCSLAILDYQKMAKGEIPKDTTPTVKVTGNELE
DGNMTLECSVNSFYPPDVITKWIESEHFKGEYKYVNGRYYPEWGRKSDYEPGEPGFPWNIKKDKDANTYS
LTDLVRTTSKMSSQLVCVVFHDTLEAQVYTCSEGCNGELYDHLYRKTEEGEGEEDEED*

FIG. 3

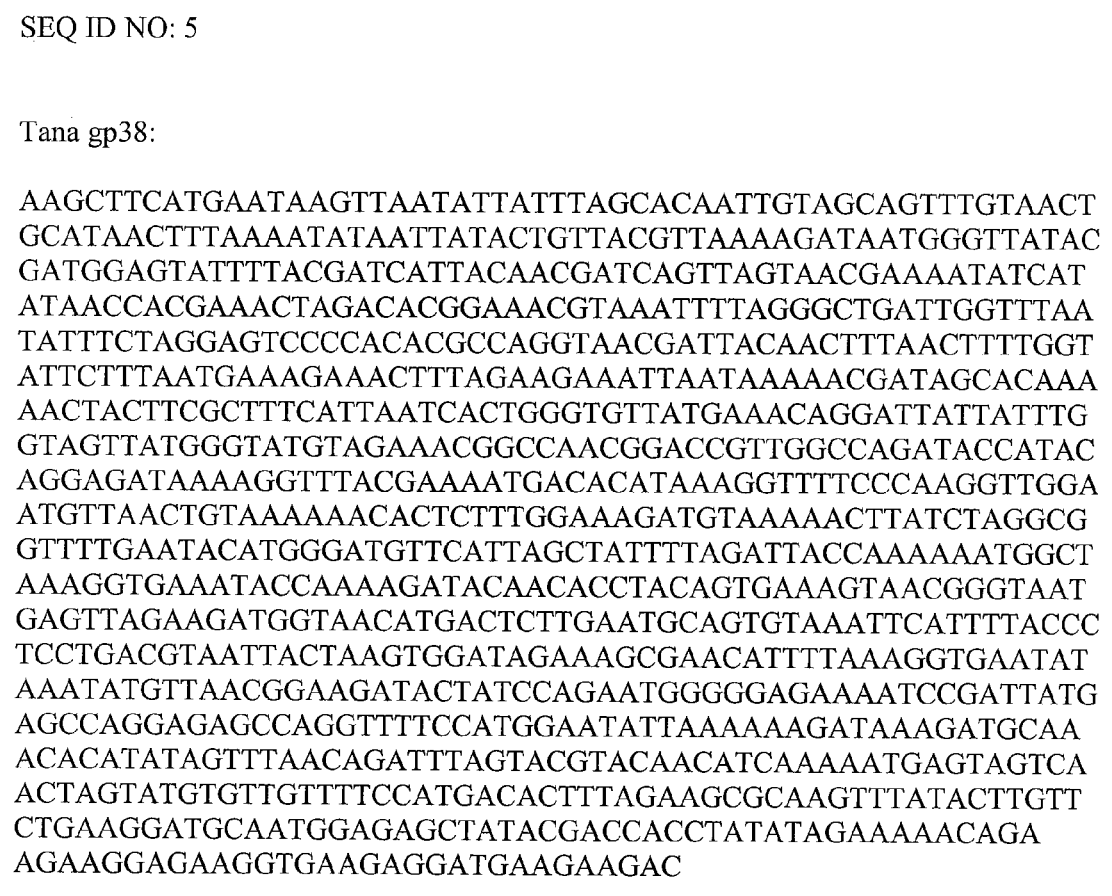

SEQ ID NO: 5

Tana gp38:

AAGCTTCATGAATAAGTTAATATTATTTAGCACAATTGTAGCAGTTTGTAACT
GCATAACTTTAAAATATAATTATACTGTTACGTTAAAAGATAATGGGTTATAC
GATGGAGTATTTTACGATCATTACAACGATCAGTTAGTAACGAAAATATCAT
ATAACCACGAAACTAGACACGGAAACGTAAATTTTAGGGCTGATTGGTTTAA
TATTTCTAGGAGTCCCCACACGCCAGGTAACGATTACAACTTTAACTTTTGGT
ATTCTTTAATGAAAGAAACTTTAGAAGAAATTAATAAAAACGATAGCACAAA
AACTACTTCGCTTTCATTAATCACTGGGTGTTATGAAACAGGATTATTATTTG
GTAGTTATGGGTATGTAGAAACGGCCAACGGACCGTTGGCCAGATACCATAC
AGGAGATAAAAGGTTTACGAAAATGACACATAAAGGTTTTCCCAAGGTTGGA
ATGTTAACTGTAAAAAACACTCTTTGGAAAGATGTAAAAACTTATCTAGGCG
GTTTTGAATACATGGGATGTTCATTAGCTATTTTAGATTACCAAAAAATGGCT
AAAGGTGAAATACCAAAAGATACAACACCTACAGTGAAAGTAACGGGTAAT
GAGTTAGAAGATGGTAACATGACTCTTGAATGCAGTGTAAATTCATTTTACCC
TCCTGACGTAATTACTAAGTGGATAGAAAGCGAACATTTTAAAGGTGAATAT
AAATATGTTAACGGAAGATACTATCCAGAATGGGGGAGAAAATCCGATTATG
AGCCAGGAGAGCCAGGTTTTCCATGGAATATTAAAAAAGATAAAGATGCAA
ACACATATAGTTTAACAGATTTAGTACGTACAACATCAAAAATGAGTAGTCA
ACTAGTATGTGTTGTTTTCCATGACACTTTAGAAGCGCAAGTTTATACTTGTT
CTGAAGGATGCAATGGAGAGCTATACGACCACCTATATAGAAAAACAGA
AGAAGGAGAAGGTGAAGAGGATGAAGAAGAC

FIG. 4

SEQ ID NO: 6

MDKLLLFSTIVAVCNCITLKYNYTVTLKDDGLYDGVFYDHYNDQLVTKISYNHETRHGNVNFRADWFNIS
RSPHTPGNDYNFNFWYSLMKETLEEINKNDSTKTTSLSLITGCYETGLLFGSYGYVETANGPLARYHTGD
KRFTKMTHKGFPKVGMLTVKNTLWKDVKAYLGGFEYMGCSLAILDYQKMAKGKIPKDTTPTVKVTGNELE
DGNMTLECTVNSFYPPDVITKWIESEHFKGEYKYVNGRYYPEWGRKSNYEPGEPGFPWNIKKDKDANTYS
LTDLVRTTSKMSSQPVCVVFHDTLEAQVYTCSEGCNGELYDHLYRKTEEGEGEEDEED*

FIG. 5

SEQ ID NO: 7

YLD gp38:

ATGGATAAGTTACTATTATTTAGCACAATTGTAGCAGTTTGTAACTGCATAAC
TTTAAAATATAATTATACTGTTACGTTAAAAGATGATGGGTTATACGATGGAG
TATTTTACGATCATTACAACGATCAGTTAGTGACGAAAATATCATATAACCAT
GAAACTAGACACGGAAACGTAAATTTTAGGGCTGATTGGTTTAATATTTCTA
GGAGTCCCCACACGCCAGGTAACGATTATAACTTTAACTTTTGGTATTCTTTA
ATGAAAGAAACTTTAGAAGAAATTAATAAAAACGATAGCACAAAAACTACTT
CGCTTTCATTAATCACTGGGTGTTATGAAACAGGATTATTATTTGGTAGTTAT
GGGTATGTAGAAACGGCCAACGGGCCGTTGGCCAGATACCATACAGGAGAT
AAAAGGTTTACGAAAATGACACATAAAGGTTTTCCCAAGGTTGGAATGTTAA
CTGTAAAAAACACTCTTTGGAAAGATGTAAAAGCTTATTTAGGCGGTTTTGA
ATATATGGATGTTCATTAGCTATTTTAGATTACCAAAAAATGGCTAAAGGTA
AAATACCAAAAGATACAACACCTACAGTGAAAGTAACGGGTAATGAGTTAG
AAGATGGTAACATGACTCTTGAATGCACTGTAAATTCATTTTACCCTCCTGAC
GTAATTACTAAGTGGATAGAAAGCGAACATTTTAAAGGTGAATATAAATATG
TTAACGGAAGATACTATCCAGAATGGGGGAGAAAATCCAATTATGAGCCAGG
AGAGCCAGGTTTTCCATGGAATATCAAAAAGATAAAGATGCAAATACATAT
AGTTTAACAGATTTAGTACGTACAACATCAAAAATGAGTAGTCAACCAGTAT
GTGTTGTTTTCCATGACACTTTAGAAGCGCAAGTTTATACTTGTTCTGAAGGA
TGCAATGGAGAGCTATACGATCACCTATATAGAAAAACAGAAGAAGGG
GAAGGTGAAGAGGATGAAGAAGACTGA

FIG. 6

SEQ ID NO: 8

MITKAIVILSIITAYVDASAFLVYNYTYTLQDDNHRYDFEVTDYFNDILIKRLKLNSETGRPELRNEPPT
WFNETKIRYYPKNNYNFMFWLNRMSETLDEINKLPETSNPYKTMSLTIGCTDLRQLQVNFGYVTVGGNIW
TRFDPKNKRFSKVRSRTFPKVGMLTVKSQHWERVMEHLGSMVTLTCPFTADDYYKISKGYIDKPVKPTVT
VTGIERGDNTTLICTFDNHYPSSVAVKWYNIEDFAPDYRYDPYVNELLPDTDYLPGEPGYPTITRRLGDK
YLFTSSPRVMVPTIMSNRIACVGFHSTLEPSIYRCVNCSGPEPVLQYQGDRRNDLEDEED

FIG. 7

SEQ ID NO: 9

Swinepox C1L

ATGATTACTAAAGCGATTGTGATATTGTCTATTATTACAGCATATGTAGATGC
TTCCGCATTCTTAGTATACAATTATACATATACTTTACAAGATGATAATCATC
GATATGACTTCGAAGTCACCGATTATTTTAATGATATACTAATAAAACGTTTA
AAACTAAATAGCGAGACAGGAAGACCAGAATTAAGAAATGAACCACCAACA
TGGTTTAATGAGACTAAGATTAGATATTATCCGAAAAATAATTATAATTTTAT
GTTCTGGCTAAATAGAATGAGTGAAACGCTAGATGAGATAAATAAACTTCCA
GAAACGAGTAATCCTTACAAGACTATGTCCTTGACAATTGGATGTACTGATCT
AAGACAACTTCAAGTAAATTTCGGTTATGTTACTGTAGGTGGTAATATATGGA
CACGATTCGACCCCAAGAATAAACGCTTTAGTAAAGTTAGATCACGTACATT
TCCAAAGGTAGGAATGTTAACTGTTAAATCACAACACTGGGAACGTGTTATG
GAACATCTTGGATCAATGGTAACATTAACATGTCCGTTTACAGCGGATGATTA
TTATAAAATTTCTAAGGGATATATAGATAAGCCAGTTAAGCCTACTGTTACAG
TTACAGGAATTGAAAGAGGAGATAATACTACATTGATATGCACATTTGATAA
TCATTATCCGTCGTCGGTCGCTGTTAAATGGTATAACATCGAGGACTTTGCTC
CGGACTATCGTTATGATCCGTACGTAAATGAATTGCTTCCTGATACGGACTAT
CTACCGGGTGAACCAGGATATCCGACTATAACTAGGAGATTAGGTGATAAAT
ATTTATTTACATCATCACCTAGGGTTATGGTACCAACTATCATGTCTAATAGA
ATAGCATGTGTTGGATTTCATAGTACGTTAGAACCAAGCATATATAGATGTGT
AAACTGCTCGGGACCTGAGCCTGTTTTACAATACCAGGGAGAT
AGAAGGAATGACTTGGAGGATGAGGAGGATTAA

FIG. 8

SEQUENCE LISTING

```
<160> NUMBER OF SEQ ID NOS: 9

<210> SEQ ID NO 1
<211> LENGTH: 26
<212> TYPE: PRT
<213> ORGANISM: Tanapox virus

<400> SEQUENCE: 1

Ile Thr Leu Lys Tyr Cys Tyr Thr Val Thr Leu Lys Asp Asn Gly Leu
1               5                   10                  15

Tyr Asp Lys Val Phe Tyr Cys His Tyr Asn
            20                  25

<210> SEQ ID NO 2
<211> LENGTH: 338
<212> TYPE: PRT
<213> ORGANISM: Yaba Monkey tumor virus

<400> SEQUENCE: 2

Met Asn Lys Leu Ile Leu Phe Ser Thr Ile Val Ala Val Cys Asn Cys
1               5                   10                  15

Ile Thr Leu Lys Tyr Asn Tyr Thr Val Thr Leu Lys Asp Asn Gly Leu
            20                  25                  30

Tyr Asp Gly Val Phe Tyr Asp His Tyr Asn Asp Gln Leu Val Thr Lys
        35                  40                  45

Ile Ser Tyr Asn His Glu Thr Arg His Gly Asn Val Asn Phe Arg Ala
    50                  55                  60

Asp Trp Phe Lys Ile Ser Arg Ser Pro His Thr Pro Gly Asn Asp Tyr
65                  70                  75                  80

Asn Phe Asn Phe Trp Tyr Ser Leu Met Lys Glu Thr Leu Glu Glu Ile
                85                  90                  95

Asn Lys Asn Asp Ser Thr Lys Thr Thr Ser Leu Ser Leu Ile Thr Gly
            100                 105                 110

Cys Tyr Glu Thr Gly Leu Leu Phe Gly Ser Tyr Gly Tyr Val Glu Thr
        115                 120                 125

Ala Asn Gly Pro Leu Ala Arg Tyr His Thr Gly Asp Lys Arg Phe Thr
    130                 135                 140

Lys Met Thr His Lys Gly Phe Pro Lys Val Gly Met Leu Thr Val Lys
145                 150                 155                 160

Asn Thr Leu Trp Lys Asp Val Lys Thr Tyr Leu Gly Gly Phe Glu Tyr
                165                 170                 175

Met Gly Cys Ser Leu Ala Ile Leu Asp Tyr Gln Lys Met Ala Lys Gly
            180                 185                 190
```

```
Glu Ile Pro Lys Asp Thr Thr Pro Thr Val Lys Val Thr Gly Asn Glu
            195                 200                 205
Leu Glu Asp Gly Asn Met Thr Leu Glu Cys Ser Val Asn Ser Phe Tyr
    210                 215                 220
Pro Pro Asp Val Ile Thr Lys Trp Ile Glu Ser Glu His Phe Lys Gly
225                 230                 235                 240
Glu Tyr Lys Tyr Val Asn Gly Arg Tyr Tyr Pro Glu Trp Gly Arg Lys
                245                 250                 255
Ser Asp Tyr Glu Pro Gly Glu Pro Gly Phe Pro Trp Asn Ile Lys Lys
            260                 265                 270
Asp Lys Asp Ala Asn Thr Tyr Ser Leu Thr Asp Leu Val Arg Thr Thr
        275                 280                 285
Ser Lys Met Ser Ser Gln Leu Val Cys Val Val Phe His Asp Thr Leu
    290                 295                 300
Glu Ala Gln Val Tyr Thr Cys Ser Glu Gly Cys Asn Gly Glu Leu Tyr
305                 310                 315                 320
Asp His Leu Tyr Arg Lys Thr Glu Glu Gly Glu Gly Glu Glu Asp Glu
                325                 330                 335
Glu Asp

<210> SEQ ID NO 3
<211> LENGTH: 1183
<212> TYPE: DNA
<213> ORGANISM: Yaba Monkey tumor virus

<400> SEQUENCE: 3
atgaataagt taattttatc gttgttgggt tttgtggcaa cttgcaattg tataacctta      60
agatataatt ataccgttac ggtaaagaat ggattatacg acggggtatt ttttgattat     120
tacaacgatc agttagtaac gaggatatca tataaccatg aaactagaca cggaaacgta     180
aattctagag cttcatggtt tgatatctct aaaagccctc atactccggg tgacgattac     240
cactttaact tttggtaccc gttaatgaaa gatactttgg agtccatcaa tagtaataaa     300
aacgaaagcg ataaatgttc ttcgttgtcg ttaattttgg ggtgttatga acgggatct     360
cttttttggga gttacggata cgttgagtca agtggcggac cgttggctag gtatagcacg     420
aaagataaaa agttttaaa aatgacagat aaaggatttc caaggttgg aatgttaacc     480
gttcatggtc ctagttggca aacagttaaa aaatacgtgg gagggtttgt gtacgctgga     540
tgtttgctag ctatttttga ttatcaaaaa atggctaaga ataacatacc tagtaatgta     600
atgccaactg ttacggtaac gggtgaggaa ctgcaagatg gtaacacaac gcttaagtgt     660
aacgtaaaat cttttaccc tccagacgta atgatcaagt ggatagaaag taatatttt     720
aacggtgaat atagatacgt taatggaaga gaatacccgg aatggggaag gcaatcagat     780
tatgagcccg gagagccagg ttttccgtta catccaaaaa aagatgacgg taaaaccact     840
tacagccttt tagattttgg tcgcactacg tcaggattaa ctagtcagtt agtttgtgtt     900
gttttccatg acacgtttga atcgcaggtt aatacatgtt ccgaagggtg tgaaggtaaa     960
ttatacgatc acctatatag aaaatcggaa gaggagacg aggttgtgga ggacgaagaa    1020
gactgaaaac aagtcgtggt ggaagctgtt ctgatcgcgc gtttacgttt ccgctagacg    1080
gaagtttgcc gcccgagagg gcgatgtttt ttttaaaaaa tgaaaaagta gatgataccg    1140
agcgatgacc gcgaaatgga ggttattaca gacggcgtgt tcg                      1183
```

<210> SEQ ID NO 4
<211> LENGTH: 338
<212> TYPE: PRT
<213> ORGANISM: Tanapox virus

<400> SEQUENCE: 4

Met Asn Lys Leu Ile Leu Phe Ser Thr Ile Val Ala Val Cys Asn Cys
1               5                   10                  15

Ile Thr Leu Lys Tyr Asn Tyr Thr Val Thr Leu Lys Asp Asn Gly Leu
            20                  25                  30

Tyr Asp Gly Val Phe Tyr Asp His Tyr Asn Asp Gln Leu Val Thr Lys
        35                  40                  45

Ile Ser Tyr Asn His Glu Thr Arg His Gly Asn Val Asn Phe Arg Ala
    50                  55                  60

Asp Trp Phe Lys Ile Ser Arg Ser Pro His Thr Pro Gly Asn Asp Tyr
65                  70                  75                  80

Asn Phe Asn Phe Trp Tyr Ser Leu Met Lys Glu Thr Leu Glu Glu Ile
                85                  90                  95

Asn Lys Asn Asp Ser Thr Lys Thr Thr Ser Leu Ser Leu Ile Thr Gly
            100                 105                 110

Cys Tyr Glu Thr Gly Leu Leu Phe Gly Ser Tyr Gly Tyr Val Glu Thr
        115                 120                 125

Ala Asn Gly Pro Leu Ala Arg Tyr His Thr Gly Asp Lys Arg Phe Thr
    130                 135                 140

Lys Met Thr His Lys Gly Phe Pro Lys Val Gly Met Leu Thr Val Lys
145                 150                 155                 160

Asn Thr Leu Trp Lys Asp Val Lys Thr Tyr Leu Gly Gly Phe Glu Tyr
                165                 170                 175

Met Gly Cys Ser Leu Ala Ile Leu Asp Tyr Gln Lys Met Ala Lys Gly
            180                 185                 190

Glu Ile Pro Lys Asp Thr Thr Pro Thr Val Lys Val Thr Gly Asn Glu
        195                 200                 205

Leu Glu Asp Gly Asn Met Thr Leu Glu Cys Ser Val Asn Ser Phe Tyr
    210                 215                 220

Pro Pro Asp Val Ile Thr Lys Trp Ile Glu Ser Glu His Phe Lys Gly
225                 230                 235                 240

Glu Tyr Lys Tyr Val Asn Gly Arg Tyr Tyr Pro Glu Trp Gly Arg Lys
                245                 250                 255

Ser Asp Tyr Glu Pro Gly Glu Pro Gly Phe Pro Trp Asn Ile Lys Lys
            260                 265                 270

Asp Lys Asp Ala Asn Thr Tyr Ser Leu Thr Asp Leu Val Arg Thr Thr
        275                 280                 285

Ser Lys Met Ser Ser Gln Leu Val Cys Val Val Phe His Asp Thr Leu
    290                 295                 300

Glu Ala Gln Val Tyr Thr Cys Ser Glu Gly Cys Asn Gly Glu Leu Tyr
305                 310                 315                 320

Asp His Leu Tyr Arg Lys Thr Glu Glu Gly Glu Gly Glu Asp Glu
                325                 330                 335

Glu Asp

<210> SEQ ID NO 5
<211> LENGTH: 1034
<212> TYPE: DNA
<213> ORGANISM: Tanapox virus

<400> SEQUENCE: 5

```
aagcttcatg aataagttaa tattatttag cacaattgta gcagtttgta actgcataac    60
tttaaaatat aattatactg ttacgttaaa agataatggg ttatacgatg gagtatttta   120
cgatcattac aacgatcagt tagtaacgaa aatatcatat aaccacgaaa ctagacacgg   180
aaacgtaaat tttagggctg attggtttaa tatttctagg agtccccaca cgccaggtaa   240
cgattacaac tttaactttt ggtattcttt aatgaaagaa actttagaag aaattaataa   300
aaacgatagc acaaaaacta cttcgctttc attaatcact gggtgttatg aaacaggatt   360
attatttggt agttatgggt atgtagaaac ggccaacgga ccgttggcca gataccatac   420
aggagataaa aggtttacga aaatgacaca taaaggtttt cccaaggttg gaatgttaac   480
tgtaaaaaac actctttgga aagatgtaaa aacttatcta ggcggttttg aatacatggg   540
atgttcatta gctatttag attaccaaaa aatggctaaa ggtgaaatac caaaagatac   600
aacacctaca gtgaaagtaa cgggtaatga gttagaagat ggtaacatga ctcttgaatg   660
cagtgtaaat tcattttacc ctcctgacgt aattactaag tggatagaaa gcgaacattt   720
taaaggtgaa tataaatatg ttaacggaag atactatcca gaatggggga gaaaatccga   780
ttatgagcca ggagagccag gttttccatg gaatattaaa aaagataaag atgcaaacac   840
atatagttta acagatttag tacgtacaac atcaaaaatg agtagtcaac tagtatgtgt   900
tgttttccat gacactttag aagcgcaagt ttatacttgt tctgaaggat gcaatggaga   960
gctatacgac cacctatata gaaaaacaga agaaggagaa ggtgaagagg atgaagaaga  1020
cggaaaccct cgag                                                    1034
```

<210> SEQ ID NO 6
<211> LENGTH: 338
<212> TYPE: PRT
<213> ORGANISM: Yaba-like disease virus

<400> SEQUENCE: 6

```
Met Asp Lys Leu Leu Leu Phe Ser Thr Ile Val Ala Val Cys Asn Cys
 1               5                  10                  15

Ile Thr Leu Lys Tyr Asn Tyr Thr Val Thr Leu Lys Asp Asp Gly Leu
            20                  25                  30

Tyr Asp Gly Val Phe Tyr Asp His Tyr Asn Asp Gln Leu Val Thr Lys
        35                  40                  45

Ile Ser Tyr Asn His Glu Thr Arg His Gly Asn Val Asn Phe Arg Ala
    50                  55                  60

Asp Trp Phe Asn Ile Ser Arg Ser Pro His Thr Pro Gly Asn Asp Tyr
65                  70                  75                  80

Asn Phe Asn Phe Trp Tyr Ser Leu Met Lys Glu Thr Leu Glu Glu Ile
                85                  90                  95

Asn Lys Asn Asp Ser Thr Lys Thr Thr Ser Leu Ser Leu Ile Thr Gly
            100                 105                 110

Cys Tyr Glu Thr Gly Leu Leu Phe Gly Ser Tyr Gly Tyr Val Glu Thr
        115                 120                 125

Ala Asn Gly Pro Leu Ala Arg Tyr His Thr Gly Asp Lys Arg Phe Thr
    130                 135                 140

Lys Met Thr His Lys Gly Phe Pro Lys Val Gly Met Leu Thr Val Lys
145                 150                 155                 160

Asn Thr Leu Trp Lys Asp Val Lys Ala Tyr Leu Gly Gly Phe Glu Tyr
                165                 170                 175

Met Gly Cys Ser Leu Ala Ile Leu Asp Tyr Gln Lys Met Ala Lys Gly
```

```
                    180             185             190
Lys Ile Pro Lys Asp Thr Thr Pro Thr Val Lys Val Thr Gly Asn Glu
            195                 200                 205

Leu Glu Asp Gly Asn Met Thr Leu Glu Cys Thr Val Asn Ser Phe Tyr
    210                 215                 220

Pro Pro Asp Val Ile Thr Lys Trp Ile Glu Ser Glu His Phe Lys Gly
225                 230                 235                 240

Glu Tyr Lys Tyr Val Asn Gly Arg Tyr Tyr Pro Glu Trp Gly Arg Lys
                245                 250                 255

Ser Asn Tyr Glu Pro Gly Glu Pro Gly Phe Pro Trp Asn Ile Lys Lys
            260                 265                 270

Asp Lys Asp Ala Asn Thr Tyr Ser Leu Thr Asp Leu Val Arg Thr Thr
        275                 280                 285

Ser Lys Met Ser Ser Gln Pro Val Cys Val Val Phe His Asp Thr Leu
    290                 295                 300

Glu Ala Gln Val Tyr Thr Cys Ser Glu Gly Cys Asn Gly Glu Leu Tyr
305                 310                 315                 320

Asp His Leu Tyr Arg Lys Thr Glu Glu Gly Glu Gly Glu Glu Asp Glu
                325                 330                 335

Glu Asp

<210> SEQ ID NO 7
<211> LENGTH: 1017
<212> TYPE: DNA
<213> ORGANISM: Yaba-like disease virus

<400> SEQUENCE: 7
atggataagt tactattatt tagcacaatt gtagcagttt gtaactgcat aactttaaaa    60
tataattata ctgttacgtt aaaagatgat gggttatacg atggagtatt ttacgatcat   120
tacaacgatc agttagtgac gaaaatatca tataaccatg aaactagaca cggaaacgta   180
aattttaggg ctgattggtt taatatttct aggagtcccc acacgccagg taacgattat   240
aactttaact tttggtattc tttaatgaaa gaaactttag aagaaattaa taaaaacgat   300
agcacaaaaa ctacttcgct ttcattaatc actgggtgtt atgaaacagg attattattt   360
ggtagttatg ggtatgtaga aacggccaac gggccgttgg ccagatacca tacaggagat   420
aaaaggttta cgaaaatgac acataaaggt tttcccaagg ttggaatgtt aactgtaaaa   480
aacactcttt ggaaagatgt aaaagcttat ttaggcggtt ttgaatatat gggatgttca   540
ttagctattt tagattacca aaaaatggct aaaggtaaaa taccaaaaga tacaacacct   600
acagtgaaag taacgggtaa tgagttagaa gatggtaaca tgactcttga atgcactgta   660
aattcatttt accctcctga cgtaattact aagtggatag aaagcgaaca ttttaaaggt   720
gaatataaat atgttaacgg aagatactat ccagaatggg ggagaaaatc caattatgag   780
ccaggagagc caggttttcc atggaatatc aaaaaagata agatgcaaa tacatatagt   840
ttaacagatt tagtacgtac aacatcaaaa atgagtagtc aaccagtatg tgttgttttc   900
catgacactt tagaagcgca agtttatact tgttctgaag gatgcaatgg agagctatac   960
gatcacctat atagaaaaac agaagaaggg gaaggtgaag aggatgaaga agactga   1017

<210> SEQ ID NO 8
<211> LENGTH: 340
<212> TYPE: PRT
<213> ORGANISM: Swinepox virus (C1L)
```

<400> SEQUENCE: 8

```
Met Ile Thr Lys Ala Ile Val Ile Leu Ser Ile Thr Ala Tyr Val
1               5                  10                  15

Asp Ala Ser Ala Phe Leu Val Tyr Asn Tyr Thr Tyr Thr Leu Gln Asp
                20                  25                  30

Asp Asn His Arg Tyr Asp Phe Glu Val Thr Asp Tyr Phe Asn Asp Ile
            35                  40                  45

Leu Ile Lys Arg Leu Lys Leu Asn Ser Glu Thr Gly Arg Pro Glu Leu
    50                  55                  60

Arg Asn Glu Pro Pro Thr Trp Phe Asn Glu Thr Lys Ile Arg Tyr Tyr
65                  70                  75                  80

Pro Lys Asn Asn Tyr Asn Phe Met Phe Trp Leu Asn Arg Met Ser Glu
                85                  90                  95

Thr Leu Asp Glu Ile Asn Lys Leu Pro Glu Thr Ser Asn Pro Tyr Lys
            100                 105                 110

Thr Met Ser Leu Thr Ile Gly Cys Thr Asp Leu Arg Gln Leu Gln Val
        115                 120                 125

Asn Phe Gly Tyr Val Thr Val Gly Gly Asn Ile Trp Thr Arg Phe Asp
    130                 135                 140

Pro Lys Asn Lys Arg Phe Ser Lys Val Arg Ser Arg Thr Phe Pro Lys
145                 150                 155                 160

Val Gly Met Leu Thr Val Lys Ser Gln His Trp Glu Arg Val Met Glu
                165                 170                 175

His Leu Gly Ser Met Val Thr Leu Thr Cys Pro Phe Thr Ala Asp Asp
            180                 185                 190

Tyr Tyr Lys Ile Ser Lys Gly Tyr Ile Asp Lys Pro Val Lys Pro Thr
        195                 200                 205

Val Thr Val Thr Gly Ile Glu Arg Gly Asp Asn Thr Thr Leu Ile Cys
    210                 215                 220

Thr Phe Asp Asn His Tyr Pro Ser Ser Val Ala Val Lys Trp Tyr Asn
225                 230                 235                 240

Ile Glu Asp Phe Ala Pro Asp Tyr Arg Tyr Asp Pro Tyr Val Asn Glu
                245                 250                 255

Leu Leu Pro Asp Thr Asp Tyr Leu Pro Gly Glu Pro Gly Tyr Pro Thr
            260                 265                 270

Ile Thr Arg Arg Leu Gly Asp Lys Tyr Leu Phe Thr Ser Ser Pro Arg
        275                 280                 285

Val Met Val Pro Thr Ile Met Ser Asn Arg Ile Ala Cys Val Gly Phe
    290                 295                 300

His Ser Thr Leu Glu Pro Ser Ile Tyr Arg Cys Val Asn Cys Ser Gly
305                 310                 315                 320

Pro Glu Pro Val Leu Gln Tyr Gln Gly Asp Arg Arg Asn Asp Leu Glu
                325                 330                 335

Asp Glu Glu Asp
            340
```

<210> SEQ ID NO 9
<211> LENGTH: 1023
<212> TYPE: DNA
<213> ORGANISM: Swinepox virus (C1L)

<400> SEQUENCE: 9

```
atgattacta aagcgattgt gatattgtct attattacag catatgtaga tgcttccgca    60
ttcttagtat acaattatac atatacttta caagatgata atcatcgata tgacttcgaa   120
```

```
                                   -continued gtcaccgatt attttaatga tatactaata aaacgtttaa aactaaatag cgagacagga      180
agaccagaat taagaaatga accaccaaca tggtttaatg agactaagat tagatattat      240
ccgaaaaata attataattt tatgttctgg ctaaatagaa tgagtgaaac gctagatgag      300
ataaataaac ttccagaaac gagtaatcct tacaagacta tgtccttgac aattggatgt      360
actgatctaa gacaacttca agtaaatttc ggttatgtta ctgtaggtgg taatatatgg      420
acacgattcg accccaagaa taaacgcttt agtaaagtta gatcacgtac atttccaaag      480
gtaggaatgt taactgttaa atcacaacac tgggaacgtg ttatgaaaca tcttggatca      540
atggtaacat taacatgtcc gtttacagcg gatgattatt ataaaatttc taagggatat      600
atagataagc cagttaagcc tactgttaca gttacaggaa ttgaaagagg agataatact      660
acattgatat gcacatttga taatcattat ccgtcgtcgg tcgctgttaa atggtataac      720
atcgaggact ttgctccgga ctatcgttat gatccgtacg taaatgaatt gcttcctgat      780
acggactatc taccgggtga accaggatat ccgactataa ctaggagatt aggtgataaa      840
tatttattta catcatcacc tagggttatg gtaccaacta tcatgtctaa tagaatagca      900
tgtgttggat ttcatagtac gttagaacca agcatatata gatgtgtaaa ctgctcggga      960
cctgagcctg ttttacaata ccagggagat agaaggaatg acttggagga tgaggaggat     1020
taa                                                                   1023
```

NUCLEIC ACID MOLECULES AND POLYPEPTIDES FOR IMMUNE MODULATION

CROSS-REFERENCE TO RELATED APPLICATION

This application is a division of U.S. Ser. No. 09/976,605 filed Oct. 11, 2001, which claims priority from U.S. Ser. No. 60/239,354, filed on Oct. 11, 2000, each of which is herein incorporated by reference.

FIELD OF THE INVENTION

The invention generally relates to immunology, and specifically relates to the identification and use of novel viral genes as immune modulators.

BACKGROUND OF THE INVENTION

Viruses propagate by living within the cells of higher-order vertebrates. Accordingly, they have evolved to specifically avoid the host immune system. Virus survival is dependent upon strategies that can evade, suppress, counteract, or otherwise circumvent host responses to a foreign antigen. These host responses are a powerful element of evolutionary pressure; all eukaryotic viruses existing today contain remnants of their battles with the host immune system, as evidenced by the presence of viral-encoded proteins that suppress the immune response or allow the virus to avoid immune system detection.

The specific strategy or strategies used by a virus varies dramatically according to its genome capacity. Viruses with small genomes ensure their survival by exploiting weaknesses or gaps in the host immune repertoire to avoid detection. Alternatively or additionally, small viral genomes replicate rapidly, effectively outpacing the host immune response. Larger DNA viruses (e.g., adenoviruses, herpesviruses, iridoviruses, and poxviruses) specifically encode proteins that function to protect the virus from immune recognition and/or clearance by the infected host. Such "subversive" viral proteins are useful therapeutics for the treatment of inflammatory and autoimmune disorders. Poxviruses, in particular, have been a rich source of such immunomodulatory proteins.

The *Yatapoxvirus* genus of poxviruses includes Tanapox virus (TPV), Yaba monkey tumor virus (YMTV), and Yaba-like disease (YLD) virus (Knight et al., *Virology* 172:116-124, 1989). Both TPV and YMTV contain a linear double-stranded, approximately 145 kbp DNA genome (Essani et al., *Microbial Pathogenesis* 17:347-353, 1994; Knight et al., supra). TPV produces a mild disease in humans, characterized by transient fever, one or more nodular skin lesions, and regional lymphadenopathy, while YMTV causes benign tumors in monkeys and humans (Paulose et al., *Microbial Pathogenesis* 25:33-41, 1998; Amano et al., *Journal of General Virology* 76:1109-1115, 1995). A 38 kDa secreted glycoprotein from TPV-induced cells has been reported to specifically bind and neutralize three human cytokines, namely interferon-γ, interleukin-2, and interleukin-5 (Essani et al., supra).

It would be useful to identify novel viral immunomodulatory genes and polypeptides for the treatment of immunological disorders.

SUMMARY OF THE INVENTION

In general, the present invention provides immunomodulatory gp38 polypeptides, nucleic acid molecules encoding these polypeptides, and therapeutic, diagnostic, and screening methods employing these polypeptides and nucleic acid molecules. The invention also provides methods for identifying compounds that modulate the biological activities of gp38 nucleic acid molecules and polypeptides, and therapeutic methods employing these compounds.

The present invention provides novel *Yatapoxvirus* immunomodulatory gp38 polypeptides, nucleic acid molecules encoding these polypeptides, and therapeutic, diagnostic, and screening methods employing these polypeptides and nucleic acid molecules. The invention also provides methods for identifying compounds that modulate the biological activities of *Yatapoxvirus* gp38 nucleic acid molecules and polypeptides, and therapeutic methods employing these compounds.

In a first aspect, the invention provides a substantially pure *Yatapoxvirus* immunomodulatory polypeptide. In preferred embodiments of the first aspect, the polypeptide can be derived from yaba monkey tumor virus or from tanapox virus. In another preferred embodiment of the first aspect, the polypeptide includes an amino acid sequence that encodes an identifiable signal sequence. In another preferred embodiment of the first aspect, the polypeptide can be a chemokine (e.g. of human interferon-γ, human interleukin-2, and human interleukin-5) binding polypeptide, a cytokine binding polypeptide, an immunomodulator, or an anti-inflammatory polypeptide. In other preferred embodiments of the first aspect, the polypeptide can be glycosylated or have anti-cytokine activity. In other preferred embodiments of the first aspect, the polypeptide may include an amino acid sequence that is substantially identical to the amino acid sequence of SEQ ID NO: 1, SEQ ID NO: 2, SEQ ID NO: 4, or SEQ ID NO: 6, or may include the amino acid sequence of SEQ ID NO: 1, SEQ ID NO: 2, SEQ ID NO 4, or SEQ ID NO: 6.

In a second aspect, the invention provides a substantially pure *Yatapoxvirus* nucleic acid molecule encoding a *Yatapoxvirus* immunomodulatory polypeptide. In preferred embodiments of the second aspect, the nucleic acid molecule can be genomic DNA, cDNA, or mRNA. In another preferred embodiment of the second aspect, the nucleic acid molecule includes a nucleotide sequence that encodes a polypeptide with an identifiable signal sequence. In other preferred embodiments of the second aspect, the nucleic acid molecule can encode a yaba monkey tumor virus polypeptide or a tanapox virus polypeptide, encode a polypeptide including an amino sequence that is substantially identical to the amino acid sequence of SEQ ID NO: 1, SEQ ID NO: 2, SEQ ID NO: 4, or SEQ ID NO: 6, or encode a polypeptide including the amino acid sequence of SEQ ID NO: 1, SEQ ID NO: 2, SEQ ID NO: 4, or SEQ ID NO: 6. In other preferred embodiments of the second aspect, the nucleic acid molecule can include a nucleotide sequence that is substantially identical to the nucleotide sequence of SEQ ID NO: 3, SEQ ID NO: 5, SEQ ID NO: 7, or SEQ ID NO: 9.

In other preferred embodiments of the second aspect, the invention provides a vector (e.g. a gene therapy vector) including the substantially pure *Yatapoxvirus* nucleic acid molecule encoding a *Yatapoxvirus* immunomodulatory polypeptide, and a cell containing this vector. The *Yatapoxvirus* nucleic acid molecule in the vector can be operably linked to regulatory sequences for expression of a *Yatapoxvirus* polypeptide and the regulatory sequences can include a promoter. The cell can be a human cell, a primate cell, or a rodent cell.

In other preferred embodiments of the second aspect, the invention provides a non-human transgenic animal containing the substantially pure *Yatapoxvirus* nucleic acid molecule encoding a *Yatapoxvirus* immunomodulatory polypeptide, and a cell from the non-human transgenic animal.

In other preferred embodiments of the second aspect, the invention provides a method detecting *Yatapoxvirus* gene or a *Yatapoxvirus* gene homolog or fragment thereof in a cell by contacting the substantially pure *Yatapoxvirus* nucleic acid molecule encoding a *Yatapoxvirus* immunomodulatory polypeptide, or a fragment thereof, where the fragment is greater than about 18 nucleotides in length, with a preparation of genomic DNA from the cell, under hybridization conditions providing detection of DNA sequences having about 50% or greater nucleotide sequence identity to SEQ ID NO: 3, SEQ ID NO: 5, SEQ ID NO: 7, or SEQ ID NO: 9.

In a third aspect, the invention provides a nucleic acid molecule having at least 50% nucleic acid sequence identity to a sequence encoding a *Yatapoxvirus* immunomodulatory polypeptide or a fragment thereof, where the fragment includes at least six amino acids and the nucleic acid molecule hybridizes under high stringency conditions to at least a portion of a *Yatapoxvirus* nucleic acid molecule. In a preferred embodiment of the third aspect, the nucleic acid molecule has 100% complementarity to a nucleic acid molecule encoding a *Yatapoxvirus* immunomodulatory polypeptide or a fragment thereof including at least six amino acids, and the nucleic acid molecule hybridizes under high stringency conditions to at least a portion of a *Yatapoxvirus* nucleic acid molecule.

In a fourth aspect, the invention provides a nucleic acid molecule, where the nucleic acid molecule includes a sequence that is antisense to the coding strand of a *Yatapoxvirus* nucleic acid molecule or a fragment thereof.

In a fifth aspect, the invention provides a non-human transgenic animal having a knockout mutation in one or both alleles encoding a polypeptide substantially identical to a *Yatapoxvirus* polypeptide.

In a sixth aspect, the invention provides an antibody that specifically binds to a *Yatapoxvirus* polypeptide, for example, a polypeptide that includes an amino acid sequence that is substantially identical to the amino acid sequence of SEQ ID NO: 1, SEQ ID NO: 2, SEQ ID NO: 4, or SEQ ID NO: 6. In a preferred embodiment of the sixth aspect, the invention provides a method of detecting a *Yatapoxvirus* polypeptide in a sample by contacting the sample with the antibody, and assaying for the binding of the antibody to the polypeptide.

In a seventh aspect, the invention provides a probe for analyzing a *Yatapoxvirus* gene or a *Yatapoxvirus* gene homolog or fragment thereof, the probe having at least 50% nucleotide sequence identity to a sequence encoding a *Yatapoxvirus* polypeptide or fragment thereof, where the fragment includes at least six amino acids, and the probe hybridizes under high stringency conditions to at least a portion of a *Yatapoxvirus* nucleic acid molecule. In a preferred embodiment of the seventh aspect, the probe has 100% complementarity to a nucleic acid molecule encoding a *Yatapoxvirus* polypeptide or fragment thereof, where the fragment includes at least six amino acids, and the probe hybridizes under high stringency conditions to at least a portion of a *Yatapoxvirus* nucleic acid molecule.

In an eighth aspect, the invention provides a method of identifying an immunomodulatory *Yatapoxvirus* gene or a *Yatapoxvirus* immunomodulatory gene homolog or fragment thereof by: (a) providing a mammalian cell sample; (b) introducing into the cell sample a candidate gene; (c) expressing the candidate gene; and (d) determining whether the candidate gene elicits an alteration in the level of immune function in the cell sample, where an alteration in the level of immune function identifies the immunomodulatory *Yatapoxvirus* gene or the *Yatapoxvirus* immunomodulatory gene homolog, or fragment thereof.

In a ninth aspect, the invention provides a method for identifying a test compound that modulates the expression or activity of a *Yatapoxvirus* polypeptide, by contacting the *Yatapoxvirus* polypeptide with the test compound, and determining the effect of the test compound on the *Yatapoxvirus* polypeptide expression or activity.

In a tenth aspect, the invention provides a method for identifying a test compound that modulates the expression or activity of a swinepox (C1L) polypeptide, by contacting the swinepox (C1L) polypeptide with the test compound, and determining the effect of the test compound on the swinepox (C1L) polypeptide expression or activity.

In an eleventh aspect, the invention provides a method of targeting proteins for secretion from a cell by attaching an identifiable signal sequence selected from a *Yatapoxvirus* polypeptide to a protein of interest, where the protein of interest is secreted from the cell.

In a twelfth aspect, the invention provides a method of targeting proteins for secretion from a cell by attaching an identifiable signal sequence selected from a swinepox (C1L) polypeptide to a protein of interest, where the protein of interest is secreted from the cell.

In a thirteenth aspect, the invention provides a method of immunomodulation in a mammal by administering to the mammal a therapeutically effective amount of a *Yatapoxvirus* polypeptide or fragment thereof, where the polypeptide has an immunomodulatory effect in the mammal.

In a fourteenth aspect, the invention provides a method of immunomodulation in a mammal by administering to the mammal a therapeutically effective amount of a swinepox (C1L) polypeptide or fragment thereof, where the polypeptide has an immunomodulatory effect in the mammal.

In a fifteenth aspect, the invention provides a method of immunomodulation in a mammal by administering to the mammal a therapeutically effective amount of a compound that modulates the activity of a *Yatapoxvirus* polypeptide, where the compound has an immunomodulatory effect in the mammal.

In a sixteenth aspect, the invention provides a method of immunomodulation in a mammal by administering to the mammal a therapeutically effective amount of a compound that modulates the activity of a swinepox (C1L) polypeptide, where the compound has an immunomodulatory effect in the mammal.

The immunomodulation of the thirteenth through sixteenth aspects can be immunosuppression, immunostimulation, cell proliferation, apoptosis, decreasing T cell stimulation, or decreasing inflammation in a mammal.

In an eighteenth aspect, the invention provides a method of treating a mammal having an immunomodulatory disorder, by administering to the mammal a therapeutically effective amount of a compound that modulates the activity of a swinepox (C1L) polypeptide, where the compound has an immunomodulatory effect in the mammal.

In a nineteenth aspect, the invention provides a pharmaceutical composition including at least one dose of a therapeutically effective amount of a *Yatapoxvirus* polypeptide or fragment thereof, in a pharmaceutically acceptable carrier, the composition being formulated for the treatment of an immunomodulatory disorder.

In a twentieth aspect, the invention provides a pharmaceutical composition including at least one dose of a therapeutically effective amount of a swinepox (C1L) polypeptide or fragment thereof, in a pharmaceutically acceptable carrier, the composition being formulated for the treatment of an immunomodulatory disorder.

In preferred embodiments of the thirteenth to twentieth aspects, the *Yatapoxvirus* polypeptide includes an amino acid sequence substantially identical to the amino acid sequence of SEQ ID NO: 1, SEQ ID NO: 2, SEQ ID NO: 4, SEQ ID NO: 6, or SEQ ID NO: 8, and fragments and analogs thereof.

In other preferred embodiments of the thirteenth to twentieth aspects, the mammal is a human. In other preferred embodiments of the thirteenth to twenty-first aspects, the mammal has a condition selected from the group consisting of acute inflammation, rheumatoid arthritis, transplant rejection, asthma, inflammatory bowel disease, uveitis, restenosis, multiple sclerosis, psoriasis, wound healing, lupus erythematosus, allergic rhinitis, atopic dermatitis, food allergies, type 1 insulin-dependent diabetes mellitus, deramatitis, meningitis, thrombotic thrombocytopenic purpura, Sjogren's syndrome, encephalitis, leukocyte adhesion deficiency, rheumatic fever, Reiter's syndrome, psoriatic arthritic, progressive systemic sclerosis, primary biliary cirrhosis, pemphigus, pemphigoid, necrotizing vasculitis, mayasthenia gravis, lupus erythmatosus, polymyositis, sarcoidosis, granulomatorsis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chromic active hepatitis, celiac disease, autoimmune complications of AIDS, atrophic gastritis, ankylosing spondylitis, Addison's disease, psoriasis, penphigus vularis, Behcet's syndrome, acute respiratory distress syndrome (ARDS), ischemic heart disease, atherosclerosis, post-dialysis syndrome, leukemia, acquired immune deficiency syndrome septic shock, lipid histiocytosis, and cancer.

In twenty-first and twenty-second aspects, the invention provides a kit for the analysis of a *Yatapoxvirus* nucleic acid molecule, the kit including a nucleic acid molecule probe for analyzing a *Yatapoxvirus* nucleic acid molecule present in a test subject, or including an antibody for analyzing a *Yatapoxvirus* polypeptide present in a test subject.

The invention provides several advantages. For example, it provides methods and reagents that can be used in the diagnosis and treatment of immune diseases that are sensitive to the bioactivities of *Yatapoxvirus* or swinepox (C1L) gp38 polypeptides. Other features and advantages of the invention will be apparent from the detailed description of the invention, the drawings, and the claims.

BRIEF DESCRIPTION OF THE DRAWINGS

FIG. 1 shows an alignment of partial amino acid sequences of gp38 from tanapox virus (SEQ ID NO: 10) and yaba monkey tumor virus (SEQ ID NO: 11).

FIG. 2 shows a partial amino acid sequence (SEQ ID NO: 11) and partial open reading frame nucleotide sequence (SEQ ID NO: 12) of gp38 from yaba monkey tumor virus (YMTV).

FIG. 3 shows the amino acid sequence of gp38 polypeptide from tanapox virus (SEQ ID NO: 4).

FIG. 4 shows the nucleic acid sequence of gp38 from tanapox virus (SEQ ID NO: 5).

FIG. 5 shows the amino acid sequence of gp38 polypeptide from yaba-like disease virus (YLDV) (SEQ ID NO: 6).

FIG. 6 shows the nucleic acid sequence of gp38 from yaba-like disease virus (YLDV) (SEQ ID NO: 7).

FIG. 7 shows the amino acid sequence of gp38 polypeptide from swinepox virus (C1L) (SEQ ID NO: 8).

FIG. 8 shows the nucleic acid sequence of gp38 from swinepox virus (C1L) (SEQ ID NO: 9).

DETAILED DESCRIPTION OF THE INVENTION

Figure 9:
FIG. 9 shows the sequence similarity of the various polypeptide amino acid sequences (SEQ ID No.s: 1, 4, 6, 2, and 8).

The invention provides gp38 polypeptides and in swinepox polypeptide, which play a role in immunomodulation, nucleic acid molecules encoding these polypeptides, and therapeutic and diagnostic methods employing these polypeptides and nucleic acid molecules. The invention also provides methods for identifying compounds that modulate the biological activities of gp38 and swinepox nucleic acid molecules and polypeptides, and therapeutic methods employing these compounds.

"Polypeptide" or "polypeptide fragment" means a chain of two or more amino acids, regardless of any post-translational modification (e.g., glycosylation, acetylation, or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A "protein" can be made up of one or more polypeptides.

"*Yatapoxvirus* gp38 immunomodulatory polypeptide" or "*Yatapoxvirus* gp38 polypeptide" means a *Yatapoxvirus* gp38 polypeptide or protein having immunomodulatory activity that is substantially identical to the polypeptide sequences described herein, or a biologically-active fragment or analog thereof. *Yatapoxviruses* have been described in, for example, Essani et al. (*Microbial Pathogenesis* 17:347-353, 1994), Knight et al. (*Virology* 172:116-124, 1989), Paulose et al. (*Microbial Pathogenesis* 25:33-41, 1998), and Amano et al. (*Journal of General Virology* 76:1109-1115, 1995), herein incorporated by reference. Specifically included in the invention are Yaba monkey tumor virus (YMTV) and tanapox virus (TPV) gp38 polypeptides.

A *Yatapoxvirus* gp38 polypeptide may also be defined as encoding a polypeptide with at least 50%, preferably at least 75%, more preferably at least 90%, and most preferably at least 95% of the biological activity, e.g., immunomodulatory or anti-inflammatory activity, compared to a reference *Yatapoxvirus* gp38 polypeptide having an amino acid sequence substantially identical to those described herein. The term *Yatapoxvirus* gp38 polypeptide includes homologs, e.g., mammalian homologs of *Yatapoxvirus* gp38 proteins as well as allelic variations, natural mutants, induced mutants, proteins encoded by DNAs that hybridize to the *Yatapoxvirus* gp38 sequences described herein under high stringency conditions, and polypeptides or proteins specifically-bound by antisera directed to a *Yatapoxvirus* gp38 polypeptide. The term also includes chimeric polypeptides that include a *Yatapoxvirus* gp38 fragment.

"Swinepox virus (C1L) gp38 immunomodulatory polypeptide" or "swinepox virus (C1L) gp38 polypeptide" means a swinepox virus (C1L) gp38 polypeptide or protein having immunomodulatory activity that is substantially identical to the polypeptide sequences described herein, or a biologically-active fragment or analog thereof.

A swinepox virus (C1L) gp38 polypeptide may also be defined as encoding a polypeptide with at least 50%, preferably at least 75%, more preferably at least 90%, and most preferably at least 95% of the biological activity, e.g., immunomodulatory or anti-inflammatory activity, compared to a reference swinepox virus (C1L) gp38 polypeptide having an amino acid sequence substantially identical to those described herein. The term swinepox virus (C1L) gp38 polypeptide includes homologs, e.g., mammalian homologs of swinepox virus (C1L) gp38 proteins as well as allelic variations, natural mutants, induced mutants, proteins encoded by DNAs that hybridize to the swinepox virus (C1L) gp38 sequences described herein under high stringency conditions, and polypeptides or proteins specifically-bound by antisera directed to a swinepox virus (C1L) gp38 polypeptide. The term also includes chimeric polypeptides that include a swinepox virus (C1L) gp38 fragment.

By "biologically-active fragment" is meant a polypeptide fragment of a *Yatapoxvirus* or swinepox virus (C1L) gp38 polypeptide that exhibits immunomodulatory properties that are at least 30%, preferably at least 50%, more preferably at least 75%, and most preferably at least 95% of the immunomodulatory properties of a full length *Yatapoxvirus* or swinepox virus (C1L) gp38 polypeptide. As used herein, the term "fragment" means at least 10 contiguous amino acids, preferably at least 30 contiguous amino acids, more preferably at least 50 contiguous amino acids, and most preferably at least 60 to 80 or more contiguous amino acids. Fragments of *Yatapoxvirus* or swinepox virus (C1L) gp38 proteins can be generated by methods known to those skilled in the art or may result from normal protein processing (e.g., removal of amino acids from the nascent polypeptide that are not required for biological activity or removal of amino acids by alternative mRNA splicing or alternative protein processing events).

By "analog" is meant any substitution, addition, or deletion in the amino acid sequence of a *Yatapoxvirus* or swinepox virus (C1L) gp38 polypeptide that exhibits properties that are at least 30%, preferably at least 50%, more preferably at least 75%, and most preferably at least 95% of the immunomodulatory properties of a *Yatapoxvirus* or swinepox virus (C1L) gp38 polypeptide from which it is derived. Analogs can differ from the naturally occurring *Yatapoxvirus* or swinepox virus (C1L) gp38 protein by amino acid sequence differences, by post-translational modifications, or by both. Analogs of the invention are substantially identical to a naturally occurring *Yatapoxvirus* or swinepox virus (C1L) gp38 sequence. Modifications include in vivo and in vitro chemical derivatization of polypeptides, e.g., acetylation, carboxylation, phosphorylation, or glycosylation. Such modifications may occur during polypeptide synthesis or processing or following treatment with isolated modifying enzymes. Analogs can also differ from the naturally occurring *Yatapoxvirus* or swinepox virus (C1L) gp38 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., *Current Protocols in Molecular Biology*, John Wiley & Sons, New York, 1994, hereby incorporated by reference). Also included are cyclized peptides molecules and analogs that contain residues other than L-amino acids, e.g., D-amino acids or non-naturally occurring or synthetic amino acids. Fragments and analogs can be generated using standard techniques, for example, solid phase peptide synthesis or polymerase chain reaction.

"*Yatapoxvirus* gp38 nucleic acid molecule" means a nucleic acid molecule, such as a genomic DNA, cDNA, or RNA (e.g., mRNA) molecule that encodes a polypeptide having the characteristics or biological activities of any *Yatapoxvirus* gp38 polypeptide described herein, or a fragment or analog thereof. A *Yatapoxvirus* gp38 nucleic acid molecule is substantially identical to a reference *Yatapoxvirus* gp38 nucleic acid molecule, as described herein.

"Swinepox virus (C1L) gp38 nucleic acid molecule" means a nucleic acid molecule, such as a genomic DNA, cDNA, or RNA (e.g., mRNA) molecule that encodes a polypeptide having the characteristics or biological activities of any swinepox virus (C1L) gp38 polypeptide described herein, or a fragment or analog thereof. A swinepox virus (C1L) gp38 nucleic acid molecule is substantially identical to a reference swinepox virus (C1L) gp38 nucleic acid molecule, as described herein.

The term "identity" is used herein to describe the relationship of the sequence of a particular nucleic acid molecule or polypeptide to the sequence of a reference molecule of the same type. For example, if a polypeptide or nucleic acid molecule has the same amino acid or nucleotide residue at a given position, compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine.

A nucleic acid molecule or polypeptide is said to be "substantially identical" to a reference molecule if it exhibits, over its entire length, at least 50% or 55% identity, preferably at least 60%, 65%, or 68% identity, more preferably at least 75% or 85% identity, and most preferably at least 90%, 95%, or 99% identity to the sequence of the reference molecule. For polypeptides, the length of comparison sequences is at least 16 amino acids, preferably at least 20 amino acids, more preferably at least 25 amino acids, and most preferably at least 35 amino acids. For nucleic acid molecules, the length of comparison sequences is at least 50 nucleotides, preferably at least 60 nucleotides, more preferably at least 75 nucleotides, and most preferably at least 110 nucleotides.

Alternatively, or additionally, two nucleic acid sequences are "substantially identical" if they hybridize under high stringency conditions. By "high stringency conditions" is meant conditions that allow hybridization comparable with the hybridization that occurs using a DNA probe of at least 500 nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually 16 nucleotides or longer for PCR or sequencing and 40 nucleotides or longer for in situ hybridization). The high stringency conditions used in these techniques are well known to those skilled in the art of molecular biology, and examples of them can be found, for example, in Ausubel et al., *Current Protocols in Molecular Biology*, John Wiley & Sons, New York, N.Y., 1998, which is hereby incorporated by reference.

By "probe" or "primer" is meant a single-stranded DNA or RNA molecule of defined sequence that can base pair to a second DNA or RNA molecule that contains a complementary sequence ("target"). The stability of the resulting hybrid depends upon the extent of the base pairing that occurs. This stability is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are well known to those skilled in the art. Probes or primers specific for *Yatapoxvirus* gp38 nucleic acid molecules, preferably, have greater than 45% sequence identity, more preferably at least 55-75% sequence identity, still more preferably at least 75-85% sequence identity, yet more preferably at least 85-99% sequence identity, and most preferably 100% sequence identity to the nucleic acid sequences encoding the amino acid sequences described herein. Probes can be detectably-labeled, either radioactively or non-radioactively, by methods that are well-known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are well known to those skilled in the art. A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably-labeling molecules are well known in the art and include, without limitation, radioactive labeling (e.g., with an isotope such as isotope, such as $^{32}$P or $^{35}$S) and nonradioactive labeling (e.g., with a fluorescent label, such as fluorescein).

"Identifiable signal sequence" means a sequence of amino acids that may be identified by homology, or biological activity, to a peptide sequence with the known function of targeting a polypeptide to a particular region of the cell. Preferably the signal sequence directs the polypeptide to the cellular membrane such that the polypeptide is secreted. Alternatively, the signal sequence may direct the polypeptide to an intracellular compartment or organelle, such as the Golgi apparatus. One of ordinary skill in the art can identify a signal sequence by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). An identifiable signal sequence can be one that is, for example, substantially identical to a sequence that results in cleavage between amino acids 17 and 18 of YMTV gp38 (SEQ ID NO: 2).

By a "substantially pure polypeptide" is meant a polypeptide (or a fragment or analog thereof) that has been separated from proteins and organic molecules that naturally accompany it. Typically, a polypeptide is substantially pure when it is at least 60%, by weight, free from the proteins and naturally-occurring organic molecules with which it is naturally associated. Preferably, the polypeptide is a *Yatapoxvirus* gp38 polypeptide that is at least 75%, more preferably at least 90%, and most preferably at least 99%, by weight, pure. A substantially pure *Yatapoxvirus* gp38 polypeptide can be obtained, for example, by extraction from a natural source (e.g., an infected mammalian cell), by expression of a recombinant nucleic acid molecule encoding a *Yatapoxvirus* gp38 polypeptide, or by chemical synthesis. Purity can be measured by any appropriate method, e.g., by column chromatography, polyacrylamide gel electrophoresis, or HPLC analysis.

A polypeptide is substantially free of naturally associated components when it is separated from those proteins and organic molecules that accompany it in its natural state. Thus, a protein that is chemically synthesized or produced in a cellular system different from the cell in which it is naturally produced is substantially free from its naturally associated components. Accordingly, substantially pure polypeptides not only include those derived from eukaryotic organisms, but also those synthesized in expression systems, for example, *E. coli* or other prokaryotes, yeast, or insect cells.

"Substantially pure nucleic acid molecule" means a nucleic acid molecule that is free of the components that naturally accompany it. For example, a substantially pure DNA is free of the genes that, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

A nucleic acid molecule that is "antisense," means a nucleic acid molecule having a sequence that is complementary to at least 75 nucleotides, and preferably at least 100, 150, or 200 nucleotides, of the coding strand of a gene or nucleic acid molecule, such as a *Yatapoxvirus* gp38 gene or nucleic acid molecule. An antisense nucleic acid molecule can be, for example, capable of preferentially lowering the production of a *Yatapoxvirus* gp38 polypeptide encoded by a *Yatapoxvirus* gp38 gene or nucleic acid molecule.

By "vector" is meant a genetically engineered plasmid or virus, derived from, for example, a bacteriophage, adenovirus, retrovirus, poxvirus, herpesvirus, or artificial chromosome, that is used to transfer a polypeptide (e.g., a *Yatapoxvirus* gp38 polypeptide) coding sequence, operably linked to a promoter, into a host cell, such that the encoded peptide or polypeptide is expressed within the host cell. A vector may be a gene therapy vector, i.e., a vector designed to transfer genetic material into the cells of a patient for a therapeutic benefit.

Vectors generally contain regulatory sequences, including promoters, operably linked to the polypeptide coding sequences. A "promoter" is a minimal nucleic acid sequence element sufficient to direct transcription. If desired, constructs of the invention can include promoter elements that are sufficient to render promoter-dependent gene expression controllable in a cell type-specific, tissue-specific, or temporal-specific manner, or inducible by external signals or agents. Such elements can be located in the 5', 3', or intron regions of a gene. Sequences are "operably linked" when a gene and one or more regulatory sequences are connected in such a way as to permit gene expression when the appropriate molecules (e.g., transcriptional activator proteins) are bound to the regulatory sequences.

By a "transgene" is meant a DNA molecule that is inserted by artifice into a cell (e.g., the nuclear genome of a cell), and is incorporated into the genome of an organism that develops from the cell. Such a transgene can be partly or entirely heterologous (i.e., foreign) to the transgenic organism, or can be a gene that is homologous to an endogenous gene of the organism. An organism or animal (e.g., a mammal, such as a mouse, rat, pig, or goat) can be said to be "transgenic" if it developed from a cell that had a transgene inserted into it by artifice.

By a "knockout mutation" is meant an artificially-induced alteration in a nucleic acid molecule (created by recombinant DNA technology or deliberate exposure to a mutagen) that reduces the biological activity of the polypeptide normally encoded therefrom by at least 80% relative to the unmutated gene. The mutation can be, without limitation, an insertion, deletion, frameshift mutation, or a missense mutation. A "knockout animal" is preferably a mammal, and more preferably a mouse, containing a knockout mutation, as defined above.

An antibody is said to "specifically bind" to a polypeptide if it recognizes and binds the polypeptide (e.g., a *Yatapoxvirus* polypeptide), but does not substantially recognize and bind other molecules (e.g., non-*Yatapoxvirus* gp38-related polypeptides) in a sample, e.g., a biological sample, that naturally includes the polypeptide. A preferred antibody binds to any *Yatapoxvirus* gp38 polypeptide sequence that is substantially identical to the polypeptide sequences shown herein, or fragments thereof.

By "sample" is meant a tissue biopsy, amniotic fluid, cell, blood, serum, urine, stool, or other specimen obtained from a patient or test subject. The sample can be analyzed to detect a mutation in a *Yatapoxvirus* gp38 gene, expression levels of a *Yatapoxvirus* gp38 gene or polypeptide, or the biological function of a *Yatapoxvirus* gp38 polypeptide, by methods that are known in the art. For example, methods such as sequencing, single-strand conformational polymorphism (SSCP) analysis, or restriction fragment length polymorphism (RFLP) analysis of PCR products derived from a patient sample can be used to detect a mutation in a *Yatapoxvirus* gp38 gene; ELISA can be used to measure levels of *Yatapoxvirus* gp38 polypeptide; and PCR can be used to measure the level of a *Yatapoxvirus* gp38 nucleic acid molecule.

"Immune function" or "immunoreactivity" refers to the ability of the immune system to respond to a foreign antigen as measured by standard assays. "Modulate" or "modulating" means the induction of a quantitative change, either by decrease or increase, in the response of a target cell, sample, or organism, as a result of an interaction with a *Yatapoxvirus* gp38 polypeptide or nucleic acid molecule or test compound. The increase or decrease is by at least 10%, preferably by at least 20%, more preferably by at least 50%, still more preferably by at least 75%, yet more preferably by at least 95% and most preferably by at least 100% relative to an untreated control organism, sample, or molecule.

"Immunomodulation" or "immunomodulatory" refers to an alteration in the overall immunoreactivity of the immune system in a mammal, or alteration in the response of a cell, relative to an untreated control of the same type, upon treatment with an agent, such as a polypeptide or nucleic acid molecule of the present invention, or fragments and analogs thereof. Immunomodulation can be assayed using immune cells, for example, B cells, T cells, antigen-presenting cells, or any other cell that is involved in immune function. Immunomodulation can also be assayed by determining expression and/or activity of immune-related genes and proteins, or immune-related compounds, such as cytokines, cytokine receptors, immunoglobulins, etc.

"Immunosuppression" refers to a decrease in the overall immunoreactivity of the immune system upon administration of an immunomodulator in comparison to the immunoreactivity of an immune system that has not been contacted with the particular immunomodulator. "Immunostimulation" refers to a increase in the overall immunoreactivity of the immune system upon administration of an immunomodulator in comparison to the immunoreactivity of an immune system that has not been contacted with the particular immunomodulator. "Decreasing T cell stimulation" means lowering the level of T cell stimulation as measured by, for example, a chromium release assay. "Decreasing inflammation" means decreasing the number of inflammatory cells (leukocytes, for example eosinophils) in the target tissue by, preferably, two-fold. By "cell proliferation" is meant the growth or reproduction of similar cells. By "apoptosis" is meant the process of cell death where a dying cell displays a set of well-characterized biochemical hallmarks which include cytolemmal blebbing, cell soma shrinkage, chromatin condensation, and DNA laddering.

"Immunomodulator" refers to an agent that induces an immunomodulatory effect or alteration (i.e., immunosuppression, immunostimulation, etc.) as measured, for example, by an alteration of virulence in mutated viruses or a variety of immunoassays well known in the art (for example, chemotaxis assays as described herein). For example, in the present invention, an immunomodulator may elicit an altered level of immune function, such that the alteration in the level of immune function identifies a *Yatapoxvirus* gp38 polypeptide. An "anti-inflammatory" agent is an immunomodulatory agent capable of decreasing the overall inflamation or immune function upon administration to an individual.

Preferably, the increase or decrease is by at least 10%, preferably by at least 20%, more preferably by at least 50%, still more preferably by at least 75%, yet more preferably by at least 95% and most preferably by at least 100% relative to an untreated control organism, sample, or molecule.

By "immunomodulatory disorder" or "immunological disorder" is meant any pathophysiological condition (i.e., a disturbance of function and/or structure of a living organism, resulting from an external source, a genetic predisposition, a physical or chemical trauma, or a combination of the above, including, but not limited to, any mammalian disease) that is characterized by an alteration in immune function.

The alteration may include, for example, a decrease in immune cell number or size, an increase in cell apoptosis or death, or a decrease in immune cell growth, survival or differentiation. Immunological disorders include any disease that involve the immune response or immunity in general. More specifically, such a disorder is a malfunction of the immune system that reduces the ability of an organism to resist foreign substances in the body (e.g.; viruses, bacteria, bacterial toxins, plant pollen, fungal spores, animal danders, medications, foods, or allogeneic or xenogeneic transplanted organs) or causes the body to produce antibodies against its own tissues (e.g., autoimmune disorders), resulting in tissue injury, or causes cancer. Immunological disorders can also occur when a malfunctioning immune system (caused by, for example, genetic defect, illness, injury, malnutrition, or medications, such as those used for chemotherapy) results in an increase in frequency or severity of infections. Immunological disorders are often accompanied by inflammation, which is the body's reaction to tissue injury, and results in the accumulation of white blood cells, macrophages, and lymphocytes at the site of injury.

Immunological or immunomodulatory disorders include, without limitation, acute inflammation, rheumatoid arthritis, transplant rejection, asthma, inflammatory bowel disease, uveitis restenosis, multiple sclerosis, psoriasis, wound healing, lupus erythematosus, and any other autoimmune or inflammatory disorder that can be recognized by one of ordinary skill in the art.

For example, other diseases related to inflammation that may be treated by methods the present invention include, but are not limited to, allergic rhinitis, atopic dermatitis and food allergies. Examples of other autoimmune disorders, where the immune system attacks the host's own tissues, include, but are not limited to, type 1 insulin-dependent diabetes mellitus, dermatitis, meningitis, thrombotic thrombocytopenic purpura, Sjogren's syndrome, encephalitis, leukocyte adhesion deficiency, rheumatic fever, Reiter's syndrome, psoriatic arthritic, progressive systemic sclerosis, primary biliary cirrhosis, pemphigus, pemphigoid, necrotizing vasculitis, myasthenia gravis, systemic lupus erythmatosus, polymyositis, sarcoidosis, granulomatorsis, vasculitis, pernicious anemia, CNS inflammatory disorder antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chromic active hepatitis, celiac disease, autoimmune complications of AIDS, atrophic gastritis, ankylosing spondylitis and Addison's disease. Other diseases related to non-malignant or immunological-related cell-proliferative diseases that may be treated by methods of the present invention include psoriasis, pemphigus vulgaris, Behcet's syndrome, acute respiratory distress syndrome (ARDS), ischemic heart disease, atherosclerosis, post-dialysis syndrome, leukemia, acquired immune deficiency syndrome septic shock and other type of acute inflammation, lipid histiocytosis, and cancer.

By "test compound" is meant a chemical, be it naturally-occurring or artificially-derived, that is assayed for its ability to act as an immunomodulator by employing one of the assay methods described herein or known in the art. Test compounds may include, for example, peptides, polypeptides, synthesized organic molecules, naturally occurring organic molecules, nucleic acid molecules, and components thereof.

"Therapeutically effective amount" as used herein in reference to dosage of a medication, refers to the administration of a specific amount of a pharmacologically active agent (e.g., a *Yatapoxvirus* gp38 polypeptide as described herein) tailored to each individual patient manifesting symptoms characteristic of an immunological disorder, or at risk for a immunological disorder. For example, a patient receiving the treatment of the present invention might be experiencing an autoimmune or inflammatory disease. A person skilled in the art will recognize that the optimal dose of a pharmaceutical agent to be administered will vary from one individual to another. Dosage in individual patients should take into account the patient's height, weight, rate of absorption and metabolism of the medication in question, the stage of the disorder to be treated, and what other pharmacological agents are administered concurrently.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline solution. Other physiologically acceptable carriers and their formulations are known to one skilled in the art and described, for example, in *Remington: The Science and Practice of Pharmacy*, ($19^{th}$ edition), ed. A. Gennaro, 1995, Mack Publishing Company, Easton, Pa.

By "treating" or "treatment" is meant the medical management of a patient with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder, preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The phrase "treatment" also includes symptomatic treatment, that is, treatment directed toward constitutional symptoms of the associated disease, pathological condition, or disorder.

By "cytokine" is meant a small molecular weight polypeptide that plays an important role in regulating the immune response, by for example, signaling adjacent cells. By "chemokine" is meant a small molecular weight ligand that is a chemoattractant for leukocytes (e.g., neutrophils, basophils, monocytes, and T cells), and is important for infiltration of lymphocytes and monocytes into sites of inflammation.

The therapeutic, diagnostic, and screening methods of the invention are first described, followed by general approaches that can be used in carrying out these methods. This description will assist those skilled in the art to better understand the invention and its principles and advantages. It is intended that this description be illustrative of the invention and not limit the scope thereof.

Therapeutic Methods Employing gp38 Nucleic Acid Molecules Polypeptides, Antibodies, And Immunomodulatory Compounds The invention includes methods of treating or preventing immunological disorders by using immunomodulatory agents. Immunomodulatory reagents include, without limitation, *Yatapoxvirus* gp38 or swinepox virus (C1L) polypeptides; *Yatapoxvirus* or swinepox virus (C1L) gp38 cDNAs, mRNAs, or antisense RNAs; *Yatapoxvirus* or swinepox virus (C1L) gp38 antibodies; and any compound that modulates *Yatapoxvirus* gp38 biological activity, expression, or stability.

*Yatapoxvirus* or swinepox virus (C1L) gp38 polypeptides identified in the present invention (or fragments or analogs thereof) that exhibit anti-cytokine activity, anti-inflammatory activity, and exhibit a decrease in leukocyte chemotaxis activity are considered particularly useful in the invention; such polypeptides may be used, for example, as therapeutics to decrease the immunoreactivity in a individual with rheumatoid arthritis. Other immunological disorders that may be treated using an immunosuppressive agent, or an agent that reduces the immune function, include acute inflammation, allergic reactions, asthmatic reactions, inflammatory bowel diseases (i.e., Crohn's Disease and ulcerative colitis), transplant rejection, and restenosis. Alternatively, a polypeptide that enhances or induces apoptosis may be used in the treatment of tumors.

Treatment or prevention of diseases resulting from an immunomodulatory disorder is accomplished, for example, by modulating the function of a immunoregulatory protein by delivering a *Yatapoxvirus* or swinepox virus (C1L) gp38 protein to the appropriate cells. It is also possible to correct an immune defect by modifying the physiological pathway (e.g., a signal transduction pathway), in which the immunoregulatory protein participates, by delivering a *Yatapoxvirus* gp38 protein or nucleic acid molecule to the appropriate cells.

Direct administration of a recombinant *Yatapoxvirus* or swinepox virus (C1L) gp38 protein, nucleic acid molecule, antibody, or compound, either to the site of a potential or actual disease-affected tissue (for example, by injection), or systemically for treatment of, for example, an autoimmune or inflammatory disorder, can be performed accordingly to any conventional recombinant protein administration technique known in the art or described herein. The actual dosage depends on a number of factors known to those of ordinary skill in the art, including the size and health of the individual patient, but generally, between 0.1 mg and 100 mg inclusive are administered per day to an adult in any pharmaceutically-acceptable formulation.

A *Yatapoxvirus* or swinepox virus (C1L) gp38 immunomodulator, antiflammatory agent, or anticarcinogen may be administered with a pharmaceutically-acceptable diluent, carrier, or excipient, at a pharmaceutically effective dose. Conventional pharmaceutical practice may be employed to provide suitable formulations or compositions to administer *Yatapoxvirus* or swinepox virus (C1L) gp38 polypeptides to patients suffering from an immunomodulatory disorder. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences, supra." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for *Yatapoxvirus* gp38 immunomodulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

*Yatapoxvirus* or *Swinepox* Virus (C1L) gp38 Gene Therapy

A *Yatapoxvirus* or swinepox virus (C1L) gp38 gene or fragment thereof can be used in immunomodulatory or anticancer gene therapy. For example, to enhance leukocyte infiltration of a tumor, a functional *Yatapoxvirus* or swinepox virus (C1L) gp38 gene or fragment thereof may be introduced into cells at the site of a tumor. In addition, *Yatapoxvirus* or swinepox virus (C1L) gp38 polypeptides that are shown to reverse autoimmune reactions can also be used in gene therapy. Alternatively, *Yatapoxvirus* or swinepox virus (C1L) gp38 polypeptides that block inflammation can be administered via gene therapy, for example, for the treatment of eosinophil-mediated inflammatory conditions.

Gene transfer is achieved using viral vectors, as well as by non-viral means. Transplantation of genes into the affected tissues of a patient can also be accomplished by transferring a *Yatapoxvirus* or swinepox virus (C1L) gp38 gene or fragment thereof into a cultivatable cell type ex vivo, after which the cell (or its descendants) is injected into a targeted tissue.

Retroviral vectors, adenoviral vectors, adeno-associated viral vectors, or other viral vectors with the appropriate tropism for *Yatapoxvirus* or swinepox virus (C1L) gp38 protein-expressing cells may be used as a gene transfer delivery system for a therapeutic *Yatapoxvirus* or swinepox virus (C1L) gp38 gene construct. Numerous vectors useful for this purpose are known (see, for example, Miller, *Human Gene Therapy* 15-14, 1990; Friedman, *Science* 244:1275-1281, 1989; Eglitis and Anderson, *BioTechniques* 6:608-614, 1988; Tolstoshev and Anderson, *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; and Miller and Rosman, *Biotechniques* 7:980-990, 1989; Le Gal La Salle et al., *Science* 259:988-990, 1993; and Johnson, *Chest* 107:77S-83S, 1995). Retroviral vectors are particularly well developed and have been used in clinical settings (Rosenberg et al., *N. Engl. J. Med* 323:370, 1990; Anderson et al., U.S. Pat. No. 5,399,346).

Non-viral approaches, for the introduction of therapeutic DNA into cells, include transfection in vitro, by means of any standard technique, including but not limited to, calcium phosphate, DEAE dextran, electroporation, protoplast fusion, and liposomes. For example, a *Yatapoxvirus* gp38 gene may be introduced into a tumor cell by lipofection (Felgner et al., *Proc. Natl. Acad. Sci.* USA 84:7413, 1987; Ono et al., *Neuroscience Lett* 117:259, 1990; Brigham et al., *Am. J. Med. Sci.* 298:278, 1989; Staubinger and Papahadjopoulos, *Meth. Enz.* 101:512, 1983); asialorosonucoid-polylysine conjugation (Wu and Wu, *J. Biol. Chem.* 263:14621, 1988; Wu et al., *J. Biol. Chem.* 264:16985, 1989); or microinjection under surgical conditions (Wolff et al., *Science* 247:1465, 1990).

For any of the above approaches, the therapeutic *Yatapoxvirus* gp38 DNA construct is preferably applied to the site of the malignancy or inflammation and cytotoxic damage (for example, by injection), but may also be applied to tissue in the vicinity of the malignancy or inflammation and cytotoxic damage, or even to a blood vessel supplying these areas.

In the gene therapy constructs, *Yatapoxvirus* or swinepox virus (C1L) gp38 cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in endothelial or epithelial cells may be used to direct *Yatapoxvirus* or swinepox virus (C1L) gp38 protein expression. Such enhancers include, without limitation, the lung specific promotors (e.g. surfactant), and gut specific regulatory sequences.

Alternatively, if a *Yatapoxvirus* or swinepox virus (C1L) gp38 genomic clone is utilized as a therapeutic construct (for example, following its isolation by hybridization with a *Yatapoxvirus* or swinepox virus (C1L) gp38 cDNA), *Yatapoxvirus* or swinepox virus (C1L) gp38 protein expression is regulated by its cognate regulatory sequences or, if desired, by regulatory sequences derived from a heterologous source, e.g., any of the promoters or regulatory elements described herein.

*Yatapoxvirus* or swinepox virus (C1L) gp38 gene therapy is also accomplished by direct administration of the *Yatapoxvirus* or swinepox virus (C1L) gp38 mRNA to a tumor. This mRNA may be produced and isolated by any standard technique, but is most readily produced by in vitro transcription using a *Yatapoxvirus* or swinepox virus (C1L) gp38 cDNA under the control of a high efficiency promoter (e.g., the T7 promoter). Administration of *Yatapoxvirus* or swinepox virus (C1L) gp38 mRNA to malignant cells is carried out by any of the methods for direct nucleic acid administration described above.

Transgenic Animals

Transgenic animals may be made using standard techniques (see for example, Gene Targeting: A Practical Approach, A. L. Joyner, ed., Oxford University Press, 1999). For example, a *Yatapoxvirus* gp38 gene may be provided using endogenous control sequences or using constitutive, tissue-specific, or inducible regulatory sequences. Transgenic animals lacking functional *Yatapoxvirus* or swinepox virus (C1L) gp38 homolog polypeptide may also be made using standard techniques. This may be done by engineering knock-out mutations in the *Yatapoxvirus* or swinepox virus (C1L) gp38 homolog gene using DNA sequences provided herein.

*Yatapoxvirus* Knockouts

Poxviruses are among the largest eukaryotic DNA viruses and have the unusual capacity to replicate autonomously in the cytoplasm of infected cells. Many poxvirus proteins have been defined as virulence factors on the basis that, when present, they confer increased pathogenicity and improve viral replication within immunocompetent hosts. When genes that encode these virulence factor proteins are deleted, the resulting virus strain generally exhibits an attenuated or altered disease phenotype (Turner, *Curr. Top. Microbiol. Immunol.*, 163:125-151, 1990; Buller, *Microbiol. Rev.*, 55:80-122, 1991; Smith, *J. Gen. Virol.*, 74:1725-1740; McFadden, Austin (Tex.): R. G. Landes Company, 1995, incorporated herein by reference). Such "knockout" *Yatapoxviruses* may assist in the elucidation of the immunomodulatory or other role of viral proteins.

Using standard virological assays (e.g., Nash et al., (1999) Immunological Review, 57:731), one of ordinary skill in the art may establish the contribution of each gene to *Yatapoxvirus* infection and the general biochemical and physiological progression of viral infection. Knockout *Yatapoxviruses* lacking a particular gene may be generated using standard molecular biological techniques (see Sambrook et al., supra; Innis et al., PCR Protocols: *A Guide to Methods and Applications*, Academic Press, San Diego, Calif., 1990; Erlich et al., *PCR Technology: Principles and Applications for DNA Amplification*, Stockton Press, New York, N.Y., 1989 each of which is incorporated herein by reference). The virulence of these knockout viruses may be assessed using standard infectivity assays well known in the art (see Nash et al., supra). For example, as mentioned above, the gp38 polypeptide of *Yatapoxviruses* (SEQ ID NOs: 1 or 2) can be useful in elucidating the mechanism used by *Yatapoxviruses* and other poxviurses to inhibit inflammation.

Diagnostic Methods Employing *Yatapoxvirus* or Swinepox Virus (C1L) gp38 Nucleic Acid Molecules, Polypeptides, and Antibodies

*Yatapoxvirus* or swinepox virus (C1L) gp38 polypeptides and nucleic acid molecules can be used in the detection or monitoring of inflammatory, autoimmune, and other conditions. For example, because *Yatapoxvirus* or swinepox virus (C1L) gp38 proteins may be involved in leukocyte chemotaxis, and because a decrease in the number of leukocytes correlates with immunosuppression, an alteration in the level of particular *Yatapoxvirus* or swinepox virus (C1L) gp38 protein production provides an indication of the prognosis of the condition. Levels of *Yatapoxvirus* or swinepox virus (C1L) gp38 protein expression may be assayed by any standard technique. For example, its expression in a biological sample (e.g., a biopsy) may be monitored by standard Northern blot analysis or may be aided by PCR (see, e.g., Ausubel et al., supra; Yap and McGee, *Nucl. Acids. Res.* 19:4294, 1991).

In yet another approach, immunoassays are used to detect or monitor *Yatapoxvirus* or swinepox virus (C1L) gp38 protein in a biological sample. *Yatapoxvirus* gp38 protein-specific polyclonal or monoclonal antibodies (produced as described herein) may be used in any standard immunoassay format (e.g., ELISA, Western blot, or RIA assay) to measure *Yatapoxvirus* or swinepox virus (C1L) gp38 polypeptide levels. A change in *Yatapoxvirus* or swinepox virus (C1L) gp38 protein production may be indicative of a particular prognosis. Examples of immunoassays are described, e.g., in Ausubel et al., supra. Immunohistochemical techniques may also be utilized for *Yatapoxvirus* or swinepox virus (C1L) gp38 protein detection. For example, a tissue sample may be obtained from a patient, and a section stained for the presence of *Yatapoxvirus* or swinepox virus (C1L) gp38 protein using an anti-*Yatapoxvirus* or swinepox virus (C1L) gp38 protein antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

Identification of Molecules that Modulate *Yatapoxvirus* or Swinepox Virus (C1L) gp38 Biological Activity or Whose Biological Activity is Modulated by *Yatapoxvirus* or Swinepox Virus (C1L) gp38 Virus Isolation of the *Yatapoxvirus* or swinepox virus (C1L) gp38 nucleic acid molecule sequence also facilitates the identification of molecules that increase or decrease a *Yatapoxvirus* gp38 or swinepox virus (C1L) polypeptide biological activity. Similarly, molecules whose activity is modulated by a *Yatapoxvirus* or swinepox virus (C1L) gp38 polypeptide biological activity can be identified. These molecules can be tested using assays described herein, e.g., chemotaxis assays. A molecule which promotes an increase in *Yatapoxvirus* or swinepox virus (C1L) gp38 protein expression or a decrease in leukocyte chemotaxis activity is considered particularly useful in the invention; such a molecule may be used, for example, as a therapeutic to decrease the immunoreactivity in a individual.

According to one approach, candidate molecules are added at varying concentrations to the culture medium of cells expressing *Yatapoxvirus* or swinepox virus (C1L) gp38 mRNA. *Yatapoxvirus* or swinepox virus (C1L) gp38 polypeptide biological activity is then measured using standard techniques. The measurement of biological activity can include the measurement of *Yatapoxvirus* or swinepox virus (C1L) gp38 polypeptide protein and nucleic acid molecule levels, or the effect of *Yatapoxvirus* or swinepox virus (C1L) gp38 polypeptide on immunomodulation If desired, the effect of candidate modulators on expression can, in the alternative, be measured at the level of *Yatapoxvi-* rus or swinepox virus (C1L) gp38 protein production using the same general approach and standard immunological detection techniques, such as western blotting or immunoprecipitation with a *Yatapoxvirus* or swinepox virus (C1L) gp38 polypeptide-specific antibody (see below).

Candidate modulators can be purified (or substantially purified) molecules or can be one component of a mixture of compounds (e.g., an extract or supernatant obtained from cells; Ausubel et al., supra). In a mixed compound assay, *Yatapoxvirus* or swinepox virus (C1L) gp38 polypeptide expression is tested against progressively smaller subsets of the candidate compound pool (e.g., produced by standard purification techniques, e.g., HPLC or FPLC) until a single compound or minimal compound mixture is demonstrated to modulate *Yatapoxvirus* or swinepox virus (C1L) gp38 polypeptide expression.

Alternatively, or in addition, candidate compounds can be screened for those that modulate *Yatapoxvirus* or swinepox virus (C1L) gp38 polypeptide activity. In this approach, the level of immunomodulation in the presence of a candidate compound is compared to the level of immunomodulation in its absence, under equivalent conditions. Again, such a screen can begin with a pool of candidate compounds, from which one or more useful modulator compounds is isolated in a step-wise fashion.

The screening assays described above can be carried out in a variety of ways that are well known to those skilled in this art. These include using *Yatapoxvirus* or swinepox virus (C1L) gp38 polypeptide variants or by using fragments of a *Yatapoxvirus* or swinepox virus (C1L) gp38 polypeptide.

A test compound that can be screened in the methods described above can be a chemical, be it naturally-occurring or artificially-derived. Such compounds can include, for example, polypeptides, synthesized organic molecules, naturally occurring organic molecules, nucleic acid molecules, and components thereof. Candidate *Yatapoxvirus* or swinepox virus (C1L) gp38. polypeptide modulators include peptide as well as non-peptide molecules (e.g., peptide or non-peptide molecules found, e.g., in a cell extract, mammalian serum, or growth medium in which mammalian cells have been cultured).

In general, novel drugs for prevention or treatment of immunomodulatory diseases are identified from large libraries of both natural products, synthetic (or semi-synthetic) extracts, and chemical libraries using methods that are well known in the art. Those skilled in the field of drug discovery and development will understand that the precise source of test extracts or compounds is not critical to the screening methods of the invention. Accordingly, virtually any number of chemical extracts or compounds can be screened using these methods. Examples of such extracts or compounds include, but are not limited to, plant-, fungal-, prokaryotic-, or animal-based extracts, fermentation broths, and synthetic compounds, as well as modifications of existing compounds.

Numerous methods are also available for generating random or directed synthesis (e.g., semi-synthesis or total synthesis) of any number of chemical compounds, including, but not limited to, saccharide-, lipid-, peptide-, and nucleic acid molecule-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound can be readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for immunological disorders can be employed whenever possible.

When a crude extract is found to regulate immunomodulation, further fractionation of the positive lead extract can be carried out to isolate chemical constituents responsible for the observed effect. Thus, the goal of the extraction, fractionation, and purification process is the careful characterization and identification of a chemical entity within the crude extract having a desired activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value can be subsequently analyzed using, for example, any of the animal models described herein.

The above approaches may also be used to inhibit the activity of the candidate compound by substituting an altered *Yatapoxvirus* or swinepox virus (C1L) gp38 polypeptide having *Yatapoxvirus* or swinepox virus (C1L) gp38 protein blocking activity (e.g., have a deletion or insertion at the amino terminus) for the *Yatapoxvirus* or swinepox virus (C1L) gp38 polypeptide described above.

Animal Models

Immunomodulators of this invention and other compounds found to be effective at the level of *Yatapoxvirus* or swinepox virus (C1L) gp38 protein expression or activity are tested in animal models, for efficacy in treating, for example, autoimmune and inflammatory diseases and cancer.

Animal models for testing the immunomodulatory effects of candidate compounds are well known in the art. Therefore, the present invention refers to a selection of animal models that can be used to test the candidate compounds of the invention. Animal models proposed for use in the present invention to test candidate compounds for their efficacy in treating autoimmune and inflammatory disorders include, but are not limited to:

Acute Inflammation:

Animal models of acute inflammation are targeted for initial and rapid drug efficacy screening, and for their potential predicative value of outcomes in chronic inflammatory diseases. The following animal models can be used to test the candidate compounds of the present invention for their efficacy in treating acute inflammation: 1) carrageenin-induced inflammation model; 2) turpentine-induced inflammation model; 3) transgenic HLAB-27 inflammation model; and 4) ear-scratch model of inflammation.

Rheumatoid Arthritis: Rat, Mouse, Rabbit

Efficacy in Rheumatoid Arthritis evaluated in: 1) various antigen-induced arthritis models in rabbit, rat, and mouse; and 2) in transgenic rheumatological models.

The molecular and cellular mechanisms of action of the candidate compounds are evaluated by testing their efficacy in influencing key intracellular mechanisms that regulate degradative processes involved in joint disease. Important molecular and cellular mechanisms that receive particular attention include signaling events regulating disease processes such as increased angiogenesis, synovial hyperplasia, and matrix metalloprotease expression. These processes have been implicated in cartilage degradation in arthritic diseases.

1. Collagen-induced Arthritis: Rat, Mouse, Rabbit

Autoimmune-mediated polyarthritis can be induced in certain strains of rodents (rat, mouse and rabbit) and non-human primates by immunizing them with native type II collagen. The collagen-induced arthritis model is widely used and well characterized. Collagen-induced arthritis is mediated by susceptibility to autoantibodies which bind to a particular region of type II collagen. The mechanism of induction is linked to MHC-class II molecules but also depends on the species of type II collagen used for immunization.

2. Ovalbumin-induced Arthritisa; Rabbit

Candidate compounds are tested for efficacy in decreasing signs and symptoms of ovalbumin arthritis. Polyarthritis is induced in rabbits by immunizing them with Ovalbumin.

3. Adjuvant-induced Arthritis: Rat, Mouse, Rabbit

Candidate compounds are tested for the efficacy in decreasing signs and symptoms of adjuvant-induced arthritis. Polyarthritis is induced in certain strains of rodents by immunizing them with Freud's Adjuvant.

4. Streptococcal Cell Wall-induced Arthritis: Rat

Candidate compounds are tested for efficacy in decreasing signs and symptoms of streptococcal cell wall-induced arthritis. Chronic, erosive polyarthritis is induced by intraperitoneal injection of an aqueous suspension of cell wall fragments isolated from group A streptococci.

Transplant Rejection (Acute and Chronic)

Efficacy in transplant rejection is evaluated in various models of graft vascular disease (GVD). GVD is the most common cause of late graft failure in solid organ transplantation. GVD or graft atherosclerosis is characterized by plaque formation and fibrosis in small vessels. The development of graft vascular disease has been associated with acute allograft rejection, ischemia-reperfusion injury, and bacterial or viral infections. The common pathway of these postoperative insults results in perivascular inflammation which triggers migration of mesenchymal cells into the vessel wall, eventually resulting in occlusion or partial occlusion of the vessel lumen.

1. Aortic Allograft Model: Rat, Rabbit, Monkey

Candidate compounds are tested for efficacy in reducing graft atherosclerosis and transplant rejection in a model of vascular injury after transplantation of aortic segments performed in certain strains of MHC mismatched rats, monkeys, and rabbits.

2. Tracheal Allograft Model: Rat, Rabbit, Monkey

Candidate compounds are tested for efficacy in reducing graft atherosclerosis and transplant rejection in a model of vascular injury after transplantation of tracheal segments performed in certain strains of MHC mismatched rats, rabbits, and monkeys.

3. Heterotopic Heart Transplant: Mouse, Rat, Monkey

A heterotropic heart transplantation is performed in MHC mismatched animals. In this model, animals are treated with cyclosporine A for only the first 7 days after transplantation are allowed to develop graft vascular disease, and are then analyzed after sacrifice at postoperative day 90.

4. Orthotopic Kidney Transplant: Mouse, Rat, Monkey

An orthotopic kidney transplantation is performed in MHC mismatched animals. In this model, animals receiving subtherapeutic doses of cyclosporine A for the first 10 days after transplantation are allowed to exhibit features of chronic renal allograft rejection in 70% of cases, and are then analyzed after sacrifice at postoperative day 90.

5. Orthotopic Lung Transplant: Rat, Monkey

Candidate compounds are tested for effectiveness in delaying or reducing signs and symptoms of organ rejection after lung whole organ transplantation in rats and monkeys.

6. Reperfusion Injury: Rat

The immediate postoperative course in clinical lung transplantation is often severely impaired by delayed graft function as a result of ischemia and reperfusion injury. Preventive efficacy of drug candidates in ischemia-reperfusion injury is evaluated using a model of acute in vivo double lung transplantation in the rat (Hausen et al., *Ann. Thorac. Surg.* 61:1714-9, 1996 incorporated herein by reference).

Restenosis

Candidate compounds are tested for efficacy in reducing atherosclerotic plaque deposition in a model of coronary restenosis after balloon angioplasty. Atherosclerotic plaque formation is critically involved in vascular occlusion and has been linked to excessive inflammatory and thrombotic response to arterial injury.

Asthma: Rodent

The effectiveness of candidate compounds in reduction of signs and symptoms of asthma is evaluated in rodent models of antigen-induced experimental airways inflammation. The models include:

1. Ovalbumin-induced Experimental Airways Inflammation: Rodent

Candidate compounds are tested for efficacy in reducing inflammatory cell components in the bronchoalveolar lavage of the lungs after aerosol challenge in ovalbumin-sensitized rodent models of experimental airways inflammation.

2. Ovalbumin-induced Allergic Sensitization in Presence of GM-CSF Transgene Expression: Mice Candidate compounds are tested for efficacy in reducing inflammatory cell components in the bronchoalveolar lavage of the lungs of mice after ovalbumin aerosol challenge in the context of local expression of GM-CSF (Staempfli et al., *J. Clin. Invest., Vol.* 102:9, 1704-1714).

Inflammatory Bowel Disease (IBD): Mice and Rats

Drug candidates are evaluated for their potential therapeutic efficacy in ulcerative colitis or Crohn's disease utilizing various models of antigen-induced and genetically-mediated spontaneous chronic intestinal inflammation in mice and rats. Examples include:

1. Dextran Sulfate Sodium Induced IBD: Mice

Chronic, irreversible clinical symptoms of IBD are induced by treating mice with an oral administration of dextran sulfate sodium.

2. Gene Deletion and Transgenic Models for IBD: Rodent

Compound efficacy will be tested in transgenic rodent lines which develop symptoms closely resembling the human elements of inflammatory bowel disease. Models include, the targeted deletion of the genes encoding IL-2, IL-10, TGF beta, T-cell receptor alpha/beta, keratin 8, Gi2 alpha. In addition, animals expressing transgenes for the human WA-B27 and HLA-B27 as well as a dominant negative construct which functionally blocks N-cadherin will be tested.

Uveitis

Drug candidates will be evaluated for efficacy in various animal models of uveitis. Key models include both, experimental autoimmune uveitis and adoptively transferred experimental autoimmune uveitis.

1. Experimental Autoimmune Uveitis (EAU)

EAU is a T-cell mediated inflammatory eye disease that can be induced in several mammalian species by immunization with ocular-specific antigens (Gery et al., *Invest. Opthalmol. Vis. Sci.*, 27: 1296-1300, 1986,. Sanui et al., *J. Exp. Med.*, 169:1947-1989, incorporated herein by reference). This experimental disease is considered a model for a family of inflammatory eye diseases in humans and has been used to examine numerous modalities before their human testing.

2. Adoptively Transferred Experimental Autoimmune Uveitis

Adoptively transferred EAU is induced through injection of lymphocytes presensitized against the retinal antigen are injected into naive syngenic recipients (McAllister et al., *J. Immunol.*, 138:1416-1420, 1987 incorporated herein by reference)

*Yatapoxvirus* or Swinepox Virus (C1L) gp38 Protein Expression

In general, *Yatapoxvirus* or swinepox virus (C1L) gp38 may be produced by transformation or transfection of a suitable host cell with all or part of a *Yatapoxvirus* or swinepox virus (C1L) gp38 protein-encoding cDNA fragment in a suitable expression vehicle.

Those skilled in the field of molecular biology will understand that any of a wide variety of expression systems may be used to provide the recombinant protein. The precise host cell used is not critical to the invention. The *Yatapoxvirus* or swinepox virus (C1L) gp38 protein may be produced in a prokaryotic host (e.g., *E. coli*) or in a eukaryotic host (yeast cells, e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual*, P. H. Pouwels et al., 1985, Supp. 1987).

One preferred expression system is the baculovirus system (using, for example, the vector pBacPAK9) available from Clontech (Pal Alto, Calif.). If desired, this system may be used in conjunction with other protein expression techniques, for example, the myc tag approach described by Evan et al. (*Mol. Cell Biol.* 5:3610-3616, 1985).

Alternatively, a *Yatapoxvirus* or swinepox virus (C1L) gp38 protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the *Yatapoxvirus* or swinepox virus (C1L) gp38 protein is cloned into an expression vector which includes the dihydrofolate reductase (DHFR) gene. Integration of the plasmid and, therefore, the *Yatapoxvirus* or swinepox virus (C1L) gp38 protein-encoding gene into the host cell chromosome is selected for by inclusion of 0.01-300 mM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant *Yatapoxvirus* or swinepox virus (C1L) gp38 protein is expressed, it is isolated, e.g., using affinity chromatography. In one example, an anti-*Yatapoxvirus* or swinepox virus (C1L) gp38 protein antibody (e.g., produced as described herein) is attached to a column and used to isolate the *Yatapoxvirus* or swinepox virus (C1L) gp38 protein. Lysis and fractionation of *Yatapoxvirus* or swinepox virus (C1L) gp38 protein-harboring cells prior to affinity chromatography are performed by standard methods (see, e.g., Ausubel et al., supra). In another example, *Yatapoxvirus* or swinepox virus (C1L) gp38 proteins are purified or substantially purified from a mixture of compounds such as an extract or supernatant obtained from cells (Ausubel et al., supra). Standard purification techniques can be used to progressively eliminate undesirable compounds from the mixture until a single compound or minimal number of effective compounds has been isolated.

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short *Yatapoxvirus* or swinepox virus (C1L) gp38 protein fragments, can also be produced by chemical synthesis (e.g., by the methods described in *Solid Phase Peptide Synthesis,* 2nd ed., 1984 The Pierce Chemical Co., Rockford, Ill.).

These general techniques of polypeptide expression and purification can also be used to produce and isolate useful *Yatapoxvirus* or swinepox virus (C1L) gp38 protein fragments or analogs (described herein).

*Yatapoxvirus* or swinepox virus (C1L) gp38 polypeptides can be attached to any one of a variety of tags. Tags can be amino acid tags or chemical tags and can be added for the purpose of purification (for example a 6-histidine tag for purification over a nickel column). Various labels can be used as means for detecting binding of a *Yatapoxvirus* or swinepox virus (C1L) gp38 protein to another protein, for example to a chemokine or a chemokine receptor. Alternatively, *Yatapoxvirus* or swinepox virus (C1L) gp38 DNAs or RNAs may be labeled for detection, for example in a hybridization assay. *Yatapoxvirus* or swinepox virus (C1L) gp38 nucleic acids or polypeptides, or derivatives thereof, may be directly or indirectly labeled, for example, with a radioisotope, a fluorescent compound, a bioluminescent compound, a chemiluminescent compound, a metal chelator or an enzyme. Those of ordinary skill in the art will know of other suitable labels or will be able to ascertain such, using routine experimentation. *Yatapoxvirus* or swinepox virus (C1L) gp38 polypeptides can also be linked to toxins. Proteins linked to toxins can be used, for example to target toxic drugs to malignant tumors if the protein has the ability localize to the tumor.

Anti-*Yatapoxvirus* or Anti-Swinepox Virus (C1L) gp38 Protein Antibodies

To generate *Yatapoxvirus* gp38 protein-specific antibodies, a *Yatapoxvirus* or swinepox virus (C1L) gp38 polypeptide coding sequence (e.g., gp38 from TPV, YMTV, or swinepox virus (C1L)) is expressed, for example, as a C-terminal fusion with glutathione S-transferase (GST) (Smith et al., *Gene* 67:31-40, 1988). The fusion protein is then purified on glutathione-Sepharose beads, eluted with glutathione cleaved with thrombin (at the engineered-cleavage site), and purified to the degree necessary for immunization of rabbits. Primary immunizations are carried out with Freud's complete adjuvant and subsequent immunizations with Freud's incomplete adjuvant. Antibody titres are monitored by Western blot and immunoprecipitation analysis using the thrombin-cleaved *Yatapoxvirus* or swinepox virus (C1L) gp38 protein fragment of the GST-*Yatapoxvirus* or swinepox virus (C1L) gp38 fusion protein. Immune sera are affinity purified using CNBr-Sepharose-coupled *Yatapoxvirus* or swinepox virus (C1L) gp38 protein. Antiserum specificity is determined using a panel of unrelated GST proteins and GST-trypsin (which was generated by PCR using known sequences).

As an alternate or adjunct immunogen to GST fusion proteins, peptides corresponding to relatively unique hydrophilic *Yatapoxvirus* or swinepox virus (C1L) gp38 proteins may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using *Yatapoxvirus* or swinepox virus (C1L) gp38 protein expressed as a GST fusion protein.

Alternatively, monoclonal antibodies may be prepared using the *Yatapoxvirus* or swinepox virus (C1L) gp38 proteins described above and standard hybridoma technology (see, e.g., Kohler et al., *Nature*, 256:495; 1975; Kohler et al., *Eur. J. Immunol.* 6:511, 1976; Kohler et al., *Eur. J. Immunol.* 6:292, 1976; Hammerling et al., In Monoclonal Antibodies and T Cell Hybridomas, Elsevier, N.Y., 1981; Ausubel et al., supra). Once produced, monoclonal antibodies are also tested for specific *Yatapoxvirus* or swinepox virus (C1L) gp38 protein recognition by Western blot or immunoprecipitation analysis (by the methods described in Ausubel et al., supra). Antibodies which specifically bind *Yatapoxvirus* or swinepox virus (C1L) gp38 proteins are considered to be useful in the invention; such antibodies may be used, e.g., in an immunoassay to monitor the level of *Yatapoxvirus* gp38 proteins produced by a mammal (for example, to determine the amount or location of a *Yatapoxvirus* or swinepox virus (C1L) gp38 protein).

Preferably, antibodies of the invention are not only produced using the whole *Yatapoxvirus* or swinepox virus (C1L) gp38 polypeptide, but using fragments of the *Yatapoxvirus* or swinepox virus (C1L) gp38 polypeptide that lie outside highly conserved regions and appear likely to be antigenic, by criteria such as high frequency of charged residues may also be used. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Antibodies to *Yatapoxvirus* or swinepox virus (C1L) proteins can be used to detect *Yatapoxvirus* or swinepox virus (C1L) proteins. In addition, the antibodies can be coupled to compounds, such as radionuclides and liposomes for diagnostic or therapeutic uses.

EXAMPLES

Cloning Additional *Yatapoxvirus*-Related gp38 Genes.

Standard techniques, such as the polymerase chain reaction (PCR) and DNA hybridization, can be used to clone *Yatapoxvirus*-related gp38 genes. *Yatapoxvirus*-Related gp38 genes and homologs can be readily identified using low-stringency DNA hybridization or low-stringency PCR with specific probes or primers. Degenerate primers *Yatapoxvirus*-related gp38 amino acid sequences can be used to clone additional *Yatapoxvirus*-related gp38 genes and homologs by RT-PCR.

Based on the amino acid sequences provided by the present invention, degenerate oligonucleotide primers containing restriction sites are synthesized. First strand cDNA is synthesized from RNA prepared from a tissue of interest and PCR is performed with an initial five cycle step, for example, at 37° C. for 60 s, followed by 25 cycles at 50° C. for 60 s (denaturation at 95° C. for 30 s and extension at 72° C. for 90 s) in order to amplify a *Yatapoxvirus*-related gp38 cDNA fragment that can be subsequently subcloned into Bluescript II KS (Stratagene). Construction of a cDNA library using poly A RNA isolated from the selected tissue is performed using Stratagene ZAP Express Vector according to the directions of the manufacturer. Potential clones are subsequently amplified and an aliquot of this cDNA library containing phage is screened with the *Yatapoxvirus* gp38 cDNA that has been $^{32}$P-labeled with Klenow enzyme. Isolated phagemids are subsequently subjected to automated sequencing on both strands using Applied Biosystems Instrumentation (model 373a) and the dye-terminator protocol. Sequence analysis is performed using software developed, for example, by the University of Wisconsin genetics computer group (Altschul, et al. *J. Mol. Biol.* 215:403-410, 1990).

*Yatapoxvirus* gp38 mRNA Expression in Different Organs.

Northern blot analysis of total RNA isolated from different mammalian tissue samples is performed to detect expression of any *Yatapoxvirus* gp38 gene, homolog or derivative. Mammalian tissues including the brain, bone marrow, skin, intestines, stomach, heart, thymus, lymph node, mammary gland, skeletal muscle, tongue, spleen, liver, testes, and kidney are analyzed. Likewise, cell lines, such as macrophages isolated and cultured from the spleen, a lung epithelial cell line, and a colon adenocarcinoma cell, are analyzed for expression of *Yatapoxvirus* gp38 mRNA.

DNA and RNA Analysis.

RNA is isolated by CsCl centrifugation in guanidine isothiocyanate (Chirgwin, et al. (1979) *Biochemistry*. 18:5294-9). Biologically active ribonucleic acid is isolated from sources enriched in ribonuclease. DNA is isolated from these gradients as well. In some cases, RNA is isolated using RNAzol (Biotecx Lab, Inc.) according to the directions of the manufacturer. Poly A RNA is enriched by elution through an oligo dT column (Pharmacia). For example, 10 µg of total RNA, 2 µg of poly A RNA, or 10 µg of restriction endonuclease cut DNA is electrophoresed in agarose, and transferred to Gene Screen (NEN Dupont) membranes. Membranes will be hybridized with $^{32}$p labeled full length cDNA or a fragment encoding the translated protein. High stringency hybridization is performed, for example, in 50% formamide, 40% dextran sulfate, 5×SSC, 1× Denhardt's solution (0.0002% (w/v) polyvinylpyrrolidone, 0.0002% (w/v) BSA, 0.0002% (w/v) Ficoll 400), 1% (w/v) SDS, 100 μg/ml denatured herring sperm DNA, and 20 mM Tris at 42° C. and blots are washed with 0.2×SSC, 0.5% SDS at 60° C. Low stringency hybridization is perfoned, for example, in 0.6M NaCl, 80 mM TrisCl, 4 mM EDTA, 0.1% (w/v) sodium pyrophosphate, 0.1% (w/v) SDS, 10× Denhardts, 100 μg/ml denatured herring sperm DNA at 50° C. and washed with 1×SSC, 0.05% SDS at 50° C. Quantitation of the intensity of band hybridization will be determined using a Phosphor-Imager (Molecular Dynamics).

*Yatapoxvirus* gp38 Gene Analysis.

A cDNA probe from the coding region of the *Yatapoxvirus* gp38 cDNA is $^{32}$P-labeled with Klenow enzyme and used to screen approximately 1×10$^6$ plaques from a mammalian genomic library (e.g., a variety of libraries are available from Stratagene, La Jolla, Calif.) under conditions of low stringency (hybridization in 0.6 M NaCl, 80 mM TrisCl, 4 mM EDTA, 0.1% sodium pyrophosphate, 0.1% SDS, 10× Denhardt's solution (0.002% polyvinyl-pyrrolidone, 0.002% BSA, 0.002% Ficoll 400), 100 μg/ml denatured herring sperm DNA at 50° C. and blots washed with 1×SSC, 0.05% SDS at 50° C.). Plaques that hybridize strongly are purifid. The genomic DNA is liberated from the phage DNA by restriction digestion with the appropriate enzymes and sub-cloned into pBlue-Script SK II (Stratagene). Any positively identified genomic fragment that hybridizes with the probe is subcloned into, for example, pBlue-Script KS II, and subjected to automated sequencing on both strands using Applied Biosystems Instrumentation (model 373a) and the dye-terminator protocol. Sequence analysis is performed using software developed by, for example, the University of Wisconsin genetics computer group Altschul et al., *J. Mol. Biol.* 215:403-410, 1990.

The *Yatapoxvirus* gp38 gene homolog chromosomal localization is determined by the analysis of any identified polymorphisms in the gene. PCR primers flanking this polymorphism will be constructed and genomic DNA is amplified by PCR. Using these primers, a size polymorphism is identified (for example, see Rowe, et al., *Mamm. Gen.* 5: 253-274, 1994).

The identified genomic fragment can be used to screen a mammalian cDNA expression library (Stratagene) under conditions of high stringency (hybridization in 50% formamide, 10% dextran sulfate, 5×SSC, 1× Denhardt's solution, 1% SDS, 100 mcg/ml denatured herring sperm DNA, and 20 mM Tris at 42° C. and blots were washed with 0.2×SSC, 0.5% SDS at 65° C.). Positive plaques are identified, purified, and phagemids are prepared according to the instructions of the library manufacturer. The inserts are completely sequenced on both strands by automated sequencing. Alignment analysis will be determined by the Clustal method using MegAlign software (DNASTAR Inc) (Higgins, et al. (1988) Gene 73, 237-244), or other standard software.

Construction and Transfection of Protein Expression Vectors.

PCR primers are designed to amplify the coding region of the *Yatapoxvirus* gp38 gene, or homolog or derivative thereof, flanked by convenient restriction sites for subsequent subcloning. PCR is performed under standard conditions using *Yatapoxvirus* gp38 cDNA pBlueScript as a template. The resulting PCR products are subsequently subcloned using, for example, a TA cloning kit (Invitrogen, San Diego, Calif.) and confirmatory sequencing is performed. *Yatapoxvirus* gp38 cDNA is subcloned into the available restriction sites of pcDNA-I/Amp (Invitrogen). Approximately 4 μg of the *Yatapoxvirus* gp38-pcDNA-I construct is transfected into 100 mm plates containing ~30% confluent COS cells using DEAE-Dextran (Lopata, et al., *Nucl. Acids Res.* 12, 5707-5717, 1984). In order to measure transfection efficiency, a replicate sample of COS cells will be transfected with a CMV promoter-placental alkaline phosphatase control plasmid (Fields-Berry et al., *Proc. Natl. Acad. Sci. U.S.A.* 89: 693-697, 1992). RNA expression is confirmed by Northern analysis using the *Yatapoxvirus* gp38 cDNA as a probe. *Yatapoxvirus* gp38-pcDNA-I transfected or mock transfected COS cell supernatant is obtained after 72 hrs of culture and stored at 4° C. In another set of transfection experiments, *Yatapoxvirus* gp38 cDNA is similarly subcloned into the available site of MoLTR-SV40 I/PA expression vector (for example, see Luster, et al., *J. Exp. Med.* 178, 1057-1065, 1993). 20 μg of linearized *Yatapoxvirus* gp38-MoLTR construct and 1 μg of linearized neomycin resistance plasmid pSV7Neo is used to transfect J558L cells by electroporation. G418 resistant cells from single wells are analyzed for *Yatapoxvirus* gp38 mRNA expression by Northern analysis. Cells expressing *Yatapoxvirus* gp38 protein or control untransfected cells (that do not express *Yatapoxvirus* gp38 protein) will be expanded in large cultures. In order to optimize the concentration of *Yatapoxvirus* gp38 protein in the supernatant, the cells are grown at high density ($1\times10^6$ cells/ml) in RPMI without FCS, cultured for 72 hrs, and the conditioned medium is concentrated 5-fold with Centricon 3000 microconcentrators (Amicon, Beverly, Mass.) before being stored.

Chemotaxis Assays. Leukocytes, for example eosinophils, are isolated. Eosinophils, in particular, can be isolated from IL-5 transgenic mice (Dent, et al., *J. Exp. Med.* 172:1425-1431, 1990). These mice develop splenomegaly, with eosinophils accounting for ~30% of the splenocytes. Eosinophils are purified from the spleen using immuno-magnetic separation to remove the contaminating splenocytes. Briefly, splenocytes are labeled with anti-Thy-1 (M5/49), anti-B220 (6B2), and anti-Lyt-2 (53-6.7). Hybridoma cell lines are obtained, for example, from American Type Culture Collection and hybridoma cell supernatants are used as a source of antibodies. The antibody labeled cells are treated with anti-serum coated-magnetic beads, the anti-serum having specificity for the isotype of the primary antibody, (M450, Dynal, Great Neck, N.Y.), and eosinophils are enriched by negative selection through a magnetic field. Macrophage cells are isolated from the peritoneal cavity of mice that have been pre-treated (2 days prior) with intraperitoneal injection of 2.9% thioglycollate (Difco, Detroit, Calif.). Peritoneal neutrophils are isolated from mice pre-treated with sodium casein (Luo, et al., *J. Immun.* 153, 4616-4624, 1994). Macrophages and neutrophils are purified by Percoll gradients (Luo, et al., *J. Immun.* 153, 4616-4624, 1994. Eosinophils or macrophages are suspended in HBSS with 0.05% BSA at $2\times10^6$ cells/ml, respectively, and 50 ml of replicate cells are placed in the top well of a 48 well micro-chemotaxis chamber (Neuro Probe, Inc, Cabin John, Md.). A polycarbonate filter with 5-μm pores are used to separate the cells from buffer (30 ml) alone or buffer containing recombinant COS cell supernatant and a positive (for example MCP-1 (Rollins, & Pober, *Am. J. Path.,* 138, 1315-1319, 1991)) and negative control (for example, supernatant from mock-transfected COS cells) so that a comparison can be made and the immunosuppressive (inhibition of chemotaxis) properties of the *Yatapoxvirus* gp38 protein assessed. Cells are incubated at 37° C. for 60 minutes (eosinophils and neutrophils) or 90 minutes (macrophages) and the cells that migrate across the filter and adhere to the bottom side of the filter are stained with Diff-Quick (Baxter Scientific, McGaw Park, Ill.). The number of cells per 400× field is counted.

Statistical Analysis. The statistical significance of differences between means is determined by analysis of variance (ANOVA). P<0.05 is considered significant. When ANOVA indicate a significant difference, the Newman-Keuls test is used to determine which groups are significantly different from each other.

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of treating an immunomodulatory disorder characterized by inflammation in a mammal, said method comprising administering to said mammal a therapeutically effective amount of a purified *Yatapoxvirus* polypeptide comprising a sequence at least 90% identical to the amino acid sequence of SEQ ID NO: 2 exclusive of identifiable signal sequence, SEQ ID NO: 4 exclusive of identifiable signal sequence, or SEQ ID NO: 6 exclusive of identifiable signal sequence, wherein said administering decreases inflammation in said mammal.

2. The method of claim 1, wherein said polypeptide is derived from yaba monkey tumor virus.

3. The method of claim 1, wherein said polypeptide is derived from tanapox virus.

4. The method of claim 1, wherein said purified *Yatapoxvirus* polypeptide comprises an identifiable signal sequence.

5. The method of claim 1, wherein said polypeptide is glycosylated.

6. The method of claim 1, wherein said polypeptide comprises an amino acid sequence that is at least 95% identical to the amino acid sequence of SEQ ID NO: 2 exclusive of identifiable signal sequence, SEQ ID NO: 4 exclusive of identifiable signal sequence, or SEQ ID NO: 6 exclusive of identifiable signal sequence.

7. The method of claim 1, wherein said mammal is a human.

8. The method of claim 1, wherein said immunomodulatory disorder is selected from the group consisting of acute inflammation, rheumatoid arthritis, transplant rejection, asthma, inflammatory bowel disease, uveitis, restenosis, lupus erythematosus, allergic rhinitis, food allergies, meningitis, rheumatic fever, CNS inflammatory disorder, habitual spontaneous abortions, glomerulonephritis, celiac disease, acute respiratory distress syndrome (ARDS), ischemic heart disease, atherosclerosis, and septic shock.

9. The method of claim 1, wherein said mammal has chronic inflammation or restenosis.

10. The method of claim 1, wherein said administering is sufficient to alleviate the symptoms of said immunomodulatory disorder.

11. The method of claim 1, wherein said inflammation is decreased by at least 10%.

12. The method of claim 11, wherein said inflammation is decreased by at least 20%.

13. The method of claim 12, wherein said inflammation is decreased by at least 50%.

14. The method of claim 1, wherein said polypeptide is at least 90% pure.

15. The method of claim 14, wherein said polypeptide is at least 99% pure.

16. The method of claim 6, wherein said polypeptide comprises the amino acid sequence of SEQ ID NO: 2 exclusive of identifiable signal sequence.

17. The method of claim 6, wherein said polypeptide comprises the amino acid sequence of SEQ ID NO: 4 exclusive of identifiable signal sequence.

18. The method of claim 6, wherein said polypeptide comprises the amino acid sequence of SEQ ID NO: 6 exclusive of identifiable signal sequence.

19. The method of claim 1, wherein said administering decreases T cell stimulation.

20. The method of claim 8, wherein said immunomodulatory disorder is selected from the group consisting of acute inflammation, rheumatoid arthritis, transplant rejection, asthma, inflammatory bowel disease, uveitis, restenosis, lupus erythematosus, allergic rhinitis, meningitis, glomerulonephritis, acute respiratory distress syndrome (ARDS), ischemic heart disease, atherosclerosis, and septic shock.

21. The method of claim 10, wherein said immunomodulatory disorder is selected from the group consisting of allergic rhinitis, asthma, inflammatory bowel disease, lupus erythematosus, restenosis, rheumatoid arthritis, transplant rejection, and uveitis.

22. A method of treating an immunomodulatory disorder characterized by inflammation in a mammal, said method comprising administering to said mammal a therapeutically effective amount of a purified *Yatapoxvirus* polypeptide comprising a sequence at least 90% identical to the amino acid sequence of SEQ ID NO: 2, SEQ ID NO: 4, or SEQ ID NO: 6, wherein said administering decreases inflammation in said mammal.

23. The method of claim 22, wherein said polypeptide is glycosylated.

24. The method of claim 22, wherein said polypeptide comprises an amino acid sequence that is at least 95% identical to the amino acid sequence of SEQ ID NO: 2, SEQ ID NO: 4, or SEQ ID NO: 6.

25. The method of claim 24, wherein said polypeptide comprises the amino acid sequence of SEQ ID NO: 2.

26. The method of claim 24, wherein said polypeptide comprises the amino acid sequence of SEQ ID NO: 4.

27. The method of claim 24, wherein said polypeptide comprises the amino acid sequence of SEQ ID NO: 6.

28. The method of claim 22, wherein said mammal is a human.

29. The method of claim 22, wherein the amino acid sequence of said polypeptide consists of an amino acid sequence at least 90% identical to the amino acid sequence of SEQ ID NO: 2, SEQ ID NO: 4, or SEQ ID NO: 6.

30. The method of claim 29, wherein the amino acid sequence of said polypeptide consists of an amino acid sequence at least 90% identical to the amino acid sequence of SEQ ID NO: 2.

31. The method of claim 29, wherein the amino acid sequence of said polypeptide consists of an amino acid sequence at least 90% identical to the amino acid sequence of SEQ ID NO: 4.

32. The method of claim 29, wherein the amino acid sequence of said polypeptide consists of an amino acid sequence at least 90% identical to the amino acid sequence of SEQ ID NO: 6.

33. The method of claim 22, wherein said immunomodulatory disorder is rheumatoid arthritis.

34. The method of claim 22, wherein said immunomodulatory disorder is psoriasis.

35. The method of claim 22, wherein said immunomodulatoiy disorder is psoriasis.

36. The method of claim 22, wherein said immunomodulatory disorder is inflammatory bowel disease.

37. The method of claim 1, wherein the amino acid sequence of said polypeptide consists of an amino acid sequence at least 90% identical to the amino acid sequence of SEQ ID NO: 2 exclusive of identifiable signal sequence, SEQ ID NO: 4 exclusive of identifiable signal sequence, or SEQ ID NO: 6 exclusive of identifiable signal sequence.

38. The method of claim 37, wherein the amino acid sequence of said polypeptide consists of an amino acid sequence of SEQ ID NO: 2 exclusive of identifiable signal sequence.

39. The method of claim 37, wherein the amino acid sequence of said polypeptide consists of the amino acid sequence of SEQ ID NO: 4 exclusive of identifiable signal sequence.

40. The method of claim 37, wherein the amino acid sequence of said polypeptide consists of the amino acid sequence of SEQ ID NO: 6 exclusive of identifiable signal sequence.

41. The method of claim 1, wherein said immunomodulatory disorder is rheumatoid arthritis.

42. The method of claim 41, wherein the amino acid sequence of said polypeptide consists of the amino acid sequence of SEQ ID NO: 4 exclusive of identifiable signal sequence.

43. The method of claim 1, wherein said immunomodulatory disorder is psoriasis.

44. The method of claim 43, wherein the amino acid sequence of said polypeptide consists of the amino acid sequence of SEQ ID NO: 4 exclusive of identifiable signal sequence.

45. The method of claim 1, wherein said immunomodulatory disorder is inflammatory bowel disease.

46. The method of claim 45, wherein the amino acid sequence of said polypeptide consists of the amino acid sequence of SEQ ID NO: 4 exclusive of identifiable signal sequence.

47. The method of claim 1, wherein said immunomodulatory disorder is transplant rejection.

48. The method of claim 47, wherein the amino acid sequence of said polypeptide consists of the amino acid sequence of SEQ ID NO: 4 exclusive of identifiable signal sequence.

49. The method of claim 1, wherein said immunomodulatory disorder is selected from the group consisting of multiple sclerosis, psoriasis, atopic dermatitis, type 1 insulin-dependent diabetes mellitus, dermatitis, Sjöigren's syndrome, encephalitis, Reiter's syndrome, psoriatic arthritis, progressive systemic sclerosis, primary biliary cirrhosis, necrotizing vasculitis, polymyositis, sarcoidosis, granulomatosis, vasculitis, Hashimoto's thyroiditis, dermatomyositis, chronic active hepatitis, atrophic gastritis, ankylosing spondylitis, and Behcet's syndrome.

* * * * *

UNITED STATES PATENT AND TRADEMARK OFFICE
CERTIFICATE OF CORRECTION

| | | |
|---|---|---|
| PATENT NO. | : 7,585,507 B2 | Page 1 of 1 |
| APPLICATION NO. | : 11/124786 | |
| DATED | : September 8, 2009 | |
| INVENTOR(S) | : McFadden et al. | |

It is certified that error appears in the above-identified patent and that said Letters Patent is hereby corrected as shown below:

On the cover page, item [*] Notice:     Subject to any disclaimer, the term of this patent is extended or adjusted under 35 USC 154(b) by 39 days Delete the phrase "by 39 days" and insert -- by 209 days --

Signed and Sealed this

Eighth Day of June, 2010

David J. Kappos
*Director of the United States Patent and Trademark Office*